(12) United States Patent
Montemagno et al.

(10) Patent No.: US 9,821,278 B2
(45) Date of Patent: Nov. 21, 2017

(54) FUNCTIONALIZED BETA-SHEET PEPTIDE STABILIZED MEMBRANE PROTEINS, CONSTRUCTS COMPRISING SAME, AND METHODS OF FORMING AND USING SAME

(71) Applicant: The Governors of the University of Alberta, Edmonton (CA)

(72) Inventors: Carlo David Montemagno, Edmonton (CA); Jeffrey Germain, Edmonton (CA); Kyle Minor, Edmonton (CA); Sinoj Abraham, Edmonton (CA); Hiofan Hoi, Edmonton (CA); Yuan He, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 15/506,654

(22) PCT Filed: Aug. 25, 2015

(86) PCT No.: PCT/CA2015/050813
§ 371 (c)(1),
(2) Date: Feb. 24, 2017

(87) PCT Pub. No.: WO2016/029308
PCT Pub. Date: Mar. 3, 2016

(65) Prior Publication Data
US 2017/0259217 A1    Sep. 14, 2017

Related U.S. Application Data

(60) Provisional application No. 62/041,587, filed on Aug. 25, 2014.

(51) Int. Cl.
*B01D 71/82* (2006.01)
*C02F 1/44* (2006.01)
(Continued)

(52) U.S. Cl.
CPC .............. *B01D 71/82* (2013.01); *C02F 1/44* (2013.01); *C07K 14/705* (2013.01); *C07K 17/08* (2013.01);
(Continued)

(58) Field of Classification Search
None
See application file for complete search history.

(56) References Cited

U.S. PATENT DOCUMENTS

| 5,955,577 A | 9/1999 | Mayo |
| 7,208,089 B2 | 4/2007 | Montemagno |

(Continued)

FOREIGN PATENT DOCUMENTS

| CA | 2607371 A1 | 11/2006 |
| WO | 2014063097 A1 | 4/2014 |

OTHER PUBLICATIONS

Avram, E., et al, "Polymers with pendant functional group. III. Polysulfones containing viologen group", Journal of Macromolecular Science, Part A. Pure and Applied Chemistry, 1997, 34(9)1701-1714.
(Continued)

*Primary Examiner* — Krishnan S Menon
(74) *Attorney, Agent, or Firm* — Oyen Wiggs Green & Mutala LLP

(57) ABSTRACT

Constructs having membrane proteins stabilized by functionalized beta-sheet peptides are provided. The constructs can be associated with or covalently linked to supports. The support can be a membrane. The membrane can be used to selectively move desired particles from one side of the membrane to the other while impeding passage of undesired particles through the membrane. Methods of making and using such constructs and membranes are provided.

20 Claims, 18 Drawing Sheets

(51) Int. Cl.
| | |
|---|---|
| C02F 101/00 | (2006.01) |
| C07K 14/705 | (2006.01) |
| C07K 17/08 | (2006.01) |
| C08G 75/23 | (2006.01) |
| C02F 101/12 | (2006.01) |
| C02F 101/16 | (2006.01) |
| C02F 101/30 | (2006.01) |
| C02F 101/38 | (2006.01) |

(52) U.S. Cl.
CPC .......... *C08G 75/23* (2013.01); *C02F 2101/12* (2013.01); *C02F 2101/16* (2013.01); *C02F 2101/306* (2013.01); *C02F 2101/308* (2013.01); *C02F 2101/38* (2013.01); *C07B 2200/11* (2013.01)

(56) References Cited

U.S. PATENT DOCUMENTS

| | | |
|---|---|---|
| 7,452,679 B2 | 11/2008 | Stupp |
| 8,247,533 B2 | 8/2012 | Kulp, III |
| 8,288,512 B2 | 10/2012 | Liebmann |
| 8,501,697 B2 | 8/2013 | Gazit |

OTHER PUBLICATIONS

Bayburt, T.H., et al, "Self-assembly of discoidal phospholipid bilayer nanoparticles with membrane scaffold proteins", Nano Letters, 2002, 2(8): 853-856.
Borgnia, M.J., et al, "Functional reconstitution and characterization of AqpZ, the *E. coli* water channel protein", Journal of Molecular Biology, 1999, 291:1169-1179.
Chae, P.S., et al, "Maltose-neopentyl glycol (MNG) amphiphiles for solubilization, stabilization and crystallization of membrane proteins", Nature Methods, 2010, 7(12):1003-1008.
Charvolin, D., et al, "The use of amphipols as universal molecular adapters to immobilize membrane proteins onto solid supports", PNAS, 2009, 106(2):405-410.
Della Pia, E.A., et al, "Functionalized amphipols: a versatile toolbox suitable for applications of membrane proteins in synthetic biology", J Membrane Biol, 2014, 247:815-826.
Erbakan, M., et al, "Molecular cloning, overexpression and characterization of a novel water channel protein from Rhodobacter sphaeroides", PLoS One, 2014, 9(1):e86830.
Ge, B., et al, "Designer amphiphilic short peptides enhance thermal stability of isolated photosystem-I", PLoS One, 2010, 2010, 5:4:e10233.
Ghosh, A.K. and E. M.V. Hoek, "Impacts of support membrane structure and chemistry on polyamide-polysulfone interfacial composite membranes", J. Mem. Sci., 2009, 336:140-148.
Gnidehou, S., et al, "Expression in *Escherichia coli* and purification of human recombinant connexin-43, a four-pass transmembrane protein", Protein Expression and Purification, 2011, 78:174-180.
Habel, J., et al, "Aquaporin-based biomimetic polymeric membranes: approaches and challenges", Membranes, 2015, 5(3):307-351.
Habibi, Y., "Key advances in the chemical modification of nanocelluloses", Chemical Society Reviews, 2014, 43:1519-1542.
Helix Nielsen, C., et al, "Robust high performance aquaporin based biomimetic membranes", Biophysical Journal, 2013, 104(2, Supp/1): 687a.
Kelly, S.M., et al, "How to study proteins by circular dichroism", Biochimica et Biophysica Acta, 2005, 1751:119-139.
Popot, J.L., et al, "Amphipols from A to Z", Annu Rev Biophys, 2011, 40:379-408.
Savage, D.F., et al, "Architecture and selectivity in aquaporins: 2.5 a X-ray structure of aquaporin Z", PLoS Biology, 2003, 1(3):334-340.
Sun, G., et al, "A novel method of aquaporinZ incorporation via binary-lipid Langumuir monolayers", Colloids and Surfaces B: Biointerfaces, 2012, 89:283-288.
Sun, G, et al, "A layer-by-layer self-assembly approach to developing an aquoporin-embedded mixed matrix membrane", RSC Adv., 2013, 3(2):473-481.
Tribet, C., et al, "Amphipols: polymers that keep membrane proteins soluble in aqueous solutions", Proc Natl Acad Sci USA, 1996, 93:15047-15050.
Yeh, J., et al, "Peptergents: peptide detergents that improve stability and functionality of a membrane protein, glycerol-3-phosphate dehydrogenase", Biochemistry, 2005, 44:16912-16919.
Zhao, X., et al, "Designer short peptide surfactants stabilize G protein-coupled receptor bovine rhodopsin", Proc Natl Acad Sci USA, 2006, 103:17707-17712.
Tang, H., et al, "Desalination by biomimetic aquaporin membranes: review of status and prospects", Desalination, 2013, 308:34-40.
Tao, H., et al, "Engineered nanostructured β-sheet peptides protect membrane proteins", Nature Methods, 2013, 10(8):759-761.
Yilmaz, G., et al, "Modifadation of polysufones by click chemistry: amphiphilic graft copolymers and their protein adsorption and cell adhesion properties", Journal of Polymer Science: Part A: Polymer Chemistry, 2010, 49:110-117.
Yilmaz, G., et al, "Polysufone based amphiphilic graft copolymers by click chemistry as bioinert membranes", Materials Science & Engineering C, 2011, 31(5):1091-1097.

| | | |
|---|---|---|
| SEQ ID NO:2 RsAqpZ | FILVFFG--CGAAVLMG--------------PQIG-------MLGISLAFGLSIVAAAYS- | 49 |
| SEQ ID NO:3 EcAqpZ | FCLVFGG--CGSAVLPAGFP---------ELGIG-------FAGVALAFGLTVLTMAFA- | 53 |
| SEQ ID NO:4 GlpF | GLLIFFG--VGCVAALKV---------------AGASFG-QWEISVIWGLGVAMAIYL- | 58 |
| SEQ ID NO:5 AqpM | FILVFFG--AGSAAVTLMIASGGTSPNPFNIGIGLLGGLGDWVAIGLAFGFAIAASIYA- | 72 |
| SEQ ID NO:6 SsAqpZ | GLFMVAAGVVGTLVFYPQSPAYQA----------IADPFLQRVVMGLGMGLTAMIIMYSP | 71 |
| SEQ ID NO:7 AQY1 | FLFLWSA--FVIAQIANQAP------E--T--PDGGSNPAQLIMISFGFGFGVMVGVFI- | 102 |
| SEQ ID NO:8 SOPIP1;2 | LLFLYIT--VATVIGHSK----------E--T-VVCGSVGLLGIAWAFGGMIFVLVYC- | 91 |
| SEQ ID NO:9 AQP1 | TLFVFIS--IGSALGFKY----------PVGN-NQTAVQDNVKVSLAFGLSIATLAQS- | 66 |
| SEQ ID NO:10 AQP4 | LIFVLLS--LGSTINWG--------------GT-EKPLPVDMVLISLCFGLSIATMVQC- | 87 |
| SEQ ID NO:11 AQP9 | FILIVLG--CGCVAQAIL---------------SRGRFGGVITINVGFSMAVAMAIYV- | 74 |
| | :: : . | |

| | | |
|---|---|---|
| RsAqpZ | LGAISGAHLNPAVSLGFLMAGRMPMAEFGGYVLAQIAGALLGSLVVFLIASG-------- | 101 |
| EcAqpZ | VGHISGGHFNPAVTIGLWAGGRFPAKEVVGYVIAQVVGGIVAAALLYLIASG-------- | 105 |
| GlpF | TAGVSGAHLNPAVTIALWLFACFDKRKVIPFIVSQVAGAFCAAALVYGLYYNLFFDFEQT | 118 |
| AqpM | LGNISGCHINPAVTIGLWSVKKFPGREVVPYIIAQLLGAAFGSFIFLQCA-G-------- | 123 |
| SsAqpZ | WGKRSGAHINPAVTLTFYRLKKIAAWDAFFYVVFQFIGGLLGVVLVAFLLQTPFT---QA | 128 |
| AQY1 | TYRVSGGNLNPAVTLALVLARAIPPFRGILMAFTQIVAGMAAAGAASAMTPG-------- | 154 |
| SOPIP1;2 | TAGISGGHINPAVTFGLFLARKVSLLRALVYMIAQCLGAICGVGLVKAFMKGP------- | 144 |
| AQP1 | VGHISGAHLNPAVTLGLLLSCQISIFRALMYIIAQCVGAIVATAILSGIT-SS------- | 118 |
| AQP4 | FGHISGGHINPAVTVAMVCTRKISIAKSVFYIAAQCLGAIIGAGILYLVT-PP------- | 139 |
| AQP9 | AGGVSGGHINPAVSLAMCLFGRMKWFKLPFYVGAQFLGAFVGAATVFGIYYDGLMSFAGG | 134 |
| | ** .:****:. : . * .. . | |

| | | |
|---|---|---|
| RsAqpZ | KAGYVLATDGLGQNGFGAGYLG-EYSMGAALIFELIATFVFVSVILAATASHVSSAS--- | 157 |
| EcAqpZ | KTGFDAAASGFASNGYGEHSPG-GYSMLSALVVELVLSAGFLLVIHGATDK---FAP--- | 158 |
| GlpF | HHIVRGSVESVDLAGTFSTYPNPHINFVQAFAVEMVITAILMGLILALTDDGNGVPR--- | 175 |
| AqpM | IG---AAT--VGGLGATAPFP--GISYWQAMLAEVVGTFLLMITIMGIA--VDERAP--- | 171 |
| SsAqpZ | PVNYV------------VTVPGKQ-GAIVACIAEYFIAVLMMSMVLFTSN--Q----PKL | 169 |
| AQY1 | -------------EIAFANALGGGASRTRGLFLEAFGTAILCLTVLMLAVEKHRA----- | 196 |
| SOPIP1;2 | ----------YNQFGGGANSVALGYNKGTALGAEIIGTFVLVYTVFSATDPKRSARDSHV | 194 |
| AQP1 | ----------LTGNSLGRNDLADGVNSGQGLGIEIIGTLQLVLCVLATTDRRRRDLG--- | 165 |
| AQP4 | ----------SVVGGLGVTMVHGNLTAGHGLLVELIITFQLVFTIFASCDSKRTDVT--- | 186 |
| AQP9 | KLLIVGENA---TAHIFATYPAPYLSLANAFADQVVATMILLIIVFAIFDSRNLGAP--- | 188 |
| | . : . : : : | |

| | | |
|---|---|---|
| RsAqpZ | TALAGLAIGLTLTGIHLVGINVTGVSVNPARSLAPALFVGG--K-----ALSDLWVFIV- | 209 |
| EcAqpZ | AGFAPIAIGLALTLIHLISIPVTNTSVNPARSTAVAIFQGG--W-----ALEQLWFFWV- | 210 |
| GlpF | GPLAPLLIGLLIAVIGASMGPLTGFAMNPARDFGPKVFAWLAGWGNVAFTGGRDIPYFLV | 235 |
| AqpM | KGFAGIIIGLTVAGIITTLGNISGSSLNPARTFGPYLNDMI--F-----AGTNLWNYYPI | 224 |
| SsAqpZ | ERFTPFFAGCLIVSYVIFESPLSGFGMNPARTVASALPSG---------IWTAIWLYFL- | 219 |
| AQY1 | TWFAPFVIGIALLIAHLICIYYTGAGLNPARSFGPAVAARS--------FPNYHWIYWL- | 247 |
| SOPIP1;2 | PILAPLPIGFAVFMVHLATIPITGTGINPARSFGAAVIFNSNK------VWDDQWIFWV- | 247 |
| AQP1 | -GSAPLAIGLSVALGHLLAIDYTGCGINPARSFGSAVITH---------NFSNHWIFWV- | 214 |
| AQP4 | -GSIALAIGFSVAIGHLFAINYTGASMNPARSFGPAVIMG---------NWENHWIYWV- | 235 |
| AQP9 | RGLEPIAIGLLIIVIASSLGLNSGCAMNPARDLSPRLFTALAGWGFEVFRAGNN--FWWI | 246 |
| | : * : : .:**** . : : | |

FUNCTIONALIZED BETA-SHEET PEPTIDE STABILIZED MEMBRANE PROTEINS, CONSTRUCTS COMPRISING SAME, AND METHODS OF FORMING AND USING SAME

REFERENCE TO RELATED APPLICATIONS

This application is a national phase entry of Patent Cooperation Treaty Patent application No. PCT/CA2015/050813, which claims priority to, and the benefit of, U.S. provisional patent application No. 62/041,587 filed 25 Aug. 2014. Both of the foregoing applications are hereby incorporated by reference herein in their entireties for all purposes.

TECHNICAL FIELD

Some embodiments of the present invention relate to functionalized β-sheet peptides and functionalized β-sheet peptide-mediated immobilization of membrane proteins. Some embodiments of the present invention relate to membrane proteins stabilized by such functionalized β-sheet peptides and their uses. Some embodiments of the present invention relate to constructs containing the protein aquaporin stabilized by such functionalized β-sheet peptides and their uses.

BACKGROUND

Membrane proteins (MPs) comprise a third of proteins encoded in genomes and perform essential functions as receptors, transporters and channels. However, their isolation and purification is challenging due to their hydrophobic nature. Conventionally, detergents are used to solubilize MPs from their native lipid environment and stabilize them in aqueous buffer[1]. However, most detergents display complicated phase behavior depending on concentration, ionic strength and the presence of other lipids and proteins. Successful methods to reconstitute membrane proteins thus rely on the unique behavior of detergents. Driven by the importance of membrane protein studies, a variety of amphiphilic reagents, including amphiphilic polymers[2], protein-based nanodiscs[3], peptide-based detergents[4], maltose neopentyl glycol detergents[5], etc., have been developed over the past decades to facilitate functional and structural studies of membrane proteins.

In an earlier work, Tao and colleagues reported the engineering of three β-sheet peptides (BPs), namely BP1, BP2 and BP3, to stabilize membrane proteins[6]. The Tao reference is incorporated herein by reference in its entirety. These β-sheet peptides are 8-amino-acid peptides with alternating polar and apolar residues and an octyl side chain at each end. The β-sheet peptides of Tao et al. share the core structure acetykoctyl)Gly-Ser-Leu-Ser-Leu-Asp-(octyl)Gly-Asp-NH$_2$ (SEQ ID NO:1) with differing numbers of N-methyl amino acids, as shown in structure (1):

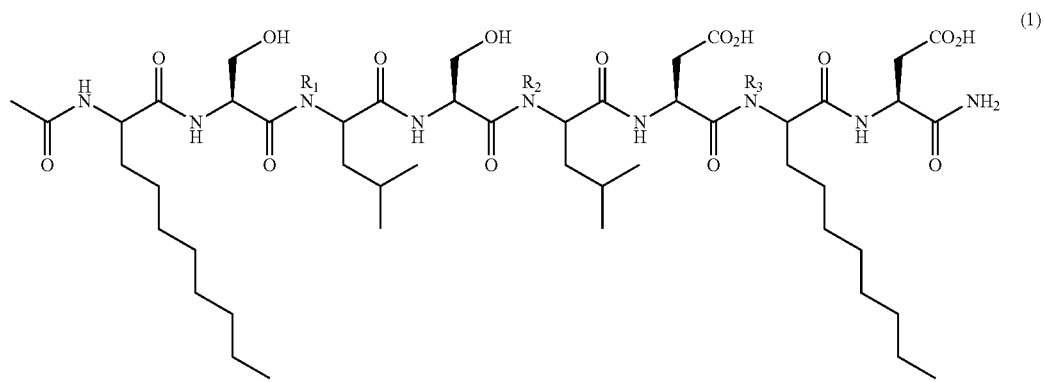

The N-methyl amino acids differ between the three constructs, BP1, BP2 and BP3 disclosed by Tao et al. as follows: for BP1 (referred to as structure (2)), $R_1=R_3=H$, $R_2=Me$. For BP2 (referred to as structure (3)), $R_1=R_2=Me$, $R_3=H$. For BP3 (referred to as structure (4)), $R_1=R_2=R_3=Me$.

Because of the special sequence design, these β-sheet peptides self-assemble into filaments in solution and restructure into a β-barrel upon association with membrane proteins (MPs). The peptides are eight amino acids in length to span the hydrophobic region of a lipid bilayer (a distance of approximately 3 nm), and, without being bound by theory, are believed to sequester the hydrophobic surfaces of the membrane protein by forming an ordered, stabilizing β-barrel-like structure. The resulting BP:MP complexes prevented membrane proteins from aggregation when diluted in detergent-free buffer. Due to the inter-strand hydrogen bond interaction, β-sheet peptides are much less likely to dissociate from the membrane proteins once the BP:MP complex has formed.

Aquaporins are a group of integral membrane proteins that conduct water through the cellular membrane with exceptional selectivity and permeability. More specifically, aquaporins selectively conduct water molecules in and out of cells, while preventing the passage of ions and other solutes. Water molecules traverse through the pore of the channel in single file. The presence of water channels increases membrane permeability to water, while the pores are impermeable to charged species, which helps to preserve a membrane's electrochemical potential difference relative to the surrounding environment.

As illustrated in FIG. 1A, aquaporins use a combination of two different mechanisms to ensure that only water molecules pass through the protein. First, the aquaporin has an hourglass-shaped channel that narrows at its middle. The narrow size of the channel provides a size restriction to help control the size of molecule that can pass through the channel. Second, the presence of a positive charge within the channel helps to prevent protons from passing through the channel. Aquaporins are made up of six transmembrane α-helices arranged in a right-handed bundle. There are five interhelical loop regions (A-E). Loops B and E are hydrophobic loops that contain a highly conserved asparagine-proline-alanine (NPA) motif, which overlaps the middle of the lipid bilayer of the membrane, forming a three-dimensional hourglass structure where water flows through the pore. Aquaporins form tetramers in the cell membrane, with each monomer acting as a water channel. Water can flow in either direction through the pores of the aquaporin, for example due to hydraulic or osmotic pressure.

Aquaporins are highly conserved. See, for example, Erbakan, M., et al. (2014). The sequence alignment carried out in this paper, shown in FIG. 1B, shows the high degree of conservation between aquaporins in diverse species including *Rhodobacter sphaeroides* ATCC 17023 (RsAqpZ, ABA78939.1, SEQ ID NO:2), *Escherichia coli* K12 (EcAqpZ, BAA08441.1, SEQ ID NO:3 and GlpF, AFH13815.1, SEQ ID NO:4), *Methanobacter marburgensis* (AqpM, ADL58146.1, SEQ ID NO:5), *Synecoccocus elongatus* (SsAqpZ, AAM82672.1 SEQ ID NO:6), *Pichia pastoris* (AQY1, CCA39392.1, SEQ ID NO:7), *Spinacia oleracea* (SOPIP2; 1, AAA99274.2, SEQ ID NO:8) and *Homo sapiens* (AQP1, NP 932766.1, SEQ ID NO:9; AQP4, AAH22286.1 SEQ ID NO:10; AQP9, NP 066190.2, SEQ ID NO:11).

Many members of the aquaporin family, for example, aquaporin Z (AqpZ) from *Escherichia coli*, are very rugged and can withstand harsh conditions without losing their function. For example, AqpZ resist denaturation from exposure to acids, voltages, detergents and heat.

Aquaporins are naturally embedded in a hydrophobic lipid bilayer environment and are normally unstable proteins that cannot function as free molecules outside of a membrane. Previous attempts have been made to use aquaporin to purify water. For example, a Langmuir-Blodgett film was devised which attempted to use aquaporin in thin monolayers to purify water, but such constructs were unstable and difficult to scale (see e.g. Sun et al., 2012). To increase stability, monolayers were tethered to support substrates and a polymer cushion was used to dampen vibration (see e.g. Sun et al., 2013); however, these constructs also proved to be unstable and difficult to produce.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a membrane configured for selectively passing desired particles across the membrane. The membrane has a support and a plurality of membrane protein molecules associated with the support. Each one of the membrane protein molecules is stabilized by a plurality of functionalized β-sheet peptides. At least some of the functionalized β-sheet peptides can be covalently linked to the support. The membrane protein molecules can form a channel in the membrane to selectively permit passage of desired particles therethrough. The membrane protein molecules can be adapted to selectively transport desired particles across the membrane. In an example embodiment, the membrane protein molecules are aquaporin, and the aquaporin molecules selectively transport water molecules across the membrane. The support can be a polysulfone polymer membrane.

One aspect of the invention provides a complex having a membrane protein stabilized by a plurality of functionalized β-sheet peptides. The complex can be immobilized on a solid support by conjugation of a functional group on at least one of the plurality of functionalized β-sheet peptides to the solid support.

In some aspects, the functionalized β-sheet peptides have the general sequence (octyl)Gly-Ser-Leu-Ser-Leu-Asp-(octyl)Gly-Asp (SEQ ID NO:1). One or more of the amino acids can be an N-methyl amino acid. The functionalized β-sheet peptides can have any suitable functional group, which can be an azide, an alkyne, an alkene, a vinyl, an azidophenyl, or a thiol in some aspects. The functionalized β-sheet peptides can be provided with a bifunctional crosslinker, which can contain a photo-reactive functional group.

One aspect of the invention provides a method of selectively passing one or more desired particles through a membrane while limiting passage of one or more contaminants through the membrane. A complex comprising a membrane protein stabilized by a plurality of functionalized β-sheet peptides is provided. The membrane protein is coupled to the membrane by reacting at least one functional group on at least one of the plurality of functionalized β-sheet peptides with the membrane. A solution containing the desired particles and the one or more contaminants is passed through the membrane so that the membrane protein selectively passes the desired particles through the membrane. In some aspects, the membrane protein is aquaporin and the desired particles are water molecules. In some aspects, the method comprises concentrating the one or more contaminants by passing a solution containing the one or more contaminants through the membrane from a first side of the membrane to a second side of the membrane to thereby concentrate the one or more contaminants on the first side of the membrane. In some such embodiments, the contaminant is a desired product.

One aspect of the invention provides a method of forming a composite structure having an immobilized membrane protein and a support. A plurality of functionalized β-sheet peptides are provided. A stable complex of the membrane protein and the functionalized β-sheet peptides is formed. The membrane protein is coupled to the support by reacting at least one functional group on at least one of the plurality of functionalized β-sheet peptides to the support to immobilize the membrane protein on the support.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 1B shows a sequence alignment showing the high degree of conservation of aquaporins from different species.

FIG. 4A shows a TEM (Transmission Electron Microscopy) image of this construct in phosphate buffered saline. Scale bar is 10 nm. FIG. 4B shows a mass spectrogram of the construct corresponding to the image shown in FIG. 4A.

FIG. 7A shows circular dichroism of AqpZ/DDM and BP1:AqpZ over 4 weeks (i.e. −1, week 1, −2, week 2, −3, week 3, and −4, week 4). FIG. 7B shows pseudo-native 12% SDS-PAGE of AqpZ/DDM and BP1:AqpZ over 3 weeks. Lanes: D: AqpZ/DDM; P: BP1:AqpZ; L: protein ladder. Arrows indicate the tetrameric AqpZ (calculated MW: 98 kDa).

FIGS. 8A-8C show the thermostability of AqpZ/DDM and BP1:AqpZ as characterized by CD. FIG. 8A shows CD spectra of AqpZ/DDM at temperatures from 20-90° C. FIG. 8B shows CD spectra of BP1:AqpZ at temperature 20-90° C. FIG. 8C shows normalized ellipticity at 192 nm plotted against temperature.

DESCRIPTION

Figure 1A:
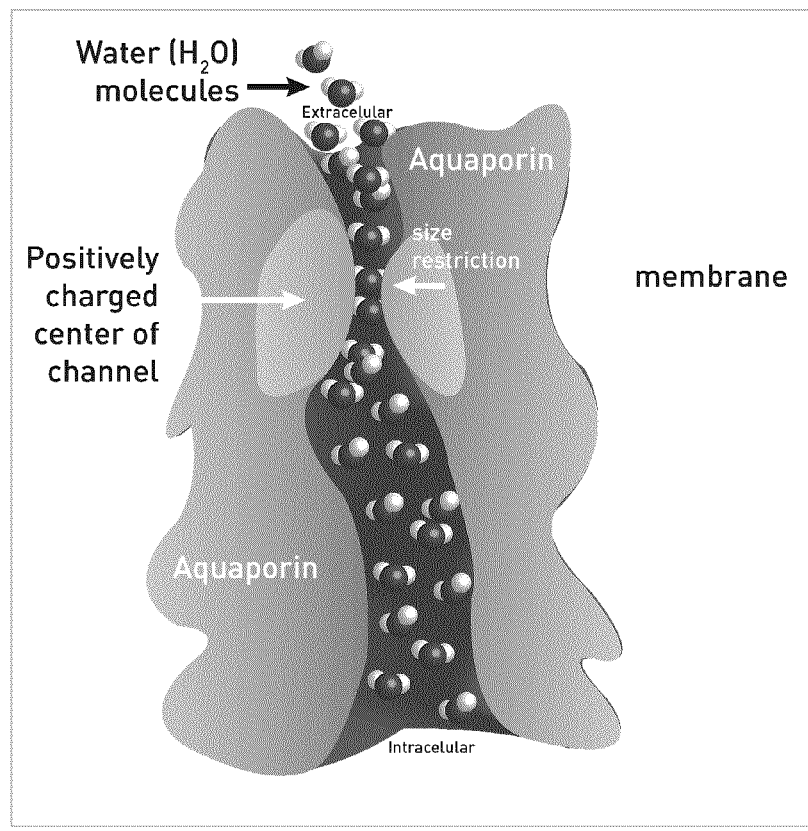
FIG. 1A shows a schematic representation of water molecules passing through an aquaporin molecule.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The intrinsic function of many membrane proteins involves recognizing and/or manipulating specific target(s). These recognizing and/or manipulating events are usually highly sensitive, as well as highly selective. Such membrane proteins are therefore excellent candidates for generating biosensors or nanomachines that take advantage of the specific function of a particular protein. A critical step to generate such biosensors or nanomachines is effective immobilization of the membrane protein on a solid support such as polymer surface, inorganic solid-state surface, etc. Nonetheless, immobilization of the hydrophobic fragile membrane proteins in their native state on a solid support in aqueous buffer remains a major challenge.

The inventors have now conceived that functionalized β-sheet peptides (FBPs) could serve as stabilizing and crosslinking agents to mediate immobilization of membrane proteins on solid supports to produce useful biosensors and/or nanomachines. In some embodiments, the membrane proteins are immobilized on a membrane to provide a composite structure wherein the membrane protein selectively transfers or allows passage of one or more desired particles from a first side of the membrane to a second side of the membrane. In some such embodiments, the membrane prevents or impedes passage of other particles from the first side of the membrane to the second side of the membrane. In some embodiments, the other particles comprise one or more contaminants. In some embodiments, the other particles comprise a component that it is desired to concentrate, and the component that it is desired to concentrate is concentrated by passing a solution containing such particles through the membrane, so that such particles are concentrated on a first side of the membrane while other components of the solution pass to the second side of the membrane.

As used herein, the term "particle" is used broadly and refers to any element or matter that it is desired to selectively pass across a membrane. For example, in some embodiments, the particles are molecules, for example, water, glycerol, carbon dioxide, sugars, organic compounds, DNA, RNA, or the like. In some embodiments, the particles are ions, for example calcium, magnesium, or the like, or ionic substances such as salts. In embodiments, the particles may be atoms or subatomic particles such as electrons.

As used herein, the term "contaminant" refers to any element or matter that it is desired to not permit to pass through a membrane. For example, in some embodiments, the contaminants are undesired particles, for example specific ions, organic molecules, waste products, or the like. For example, in embodiments in which it is desired to provide purified water, the contaminant may be sodium chloride found in seawater, or the byproduct of an industrial process or agricultural operation that it is desired to remove from the water. In some embodiments, the contaminants are particles that are desired to be concentrated, for example by allowing water to pass out of a solution while containing a particle to be concentrated on a first side of the membrane to thereby concentrate the particle to be concentrated. Thus, the word "contaminants" as used herein is not limited to undesired particles, but could include a particle that it is desired to prevent from passing through a membrane in order to concentrate and/or harvest that particle.

One aspect of the invention provides functionalized β-sheet peptides (FBPs). In some embodiments, the functionalized β-sheet peptide (FBP) comprises a β-sheet peptide (BP) and a functional group which is attached to said β-sheet peptide (BP). For example, such a functionalized β-sheet peptide could be generated by attaching a functional group to a β-sheet peptide. In some embodiments, the functional group may be attached to a C-terminal end of the β-sheet peptide, or to an N-terminal end of the β-sheet peptide. In other embodiments the functional group may be attached to a moiety located between the ends of the peptide. In some embodiments multiple functional groups may be attached to the β-sheet peptide. For example, the functional group may comprise an azide, an alkyne, an alkene, a vinyl, an azidophenyl, a thiol, or some other suitable functional group. In some embodiments, the functionalized β-sheet peptides are synthesized by conventional solid-phase peptide synthesis, incorporating modified amino acids bearing a desired functional group at a desired point in the peptide sequence.

In some embodiments, the functionalized β-sheet peptide may comprise a β-sheet peptide which is different from the three β-sheet peptides disclosed in the Tao reference. The β-sheet peptide may, for example, be any suitable β-sheet peptide of any suitable length having alternating hydrophobic and hydrophilic residues.

Figure 2A:
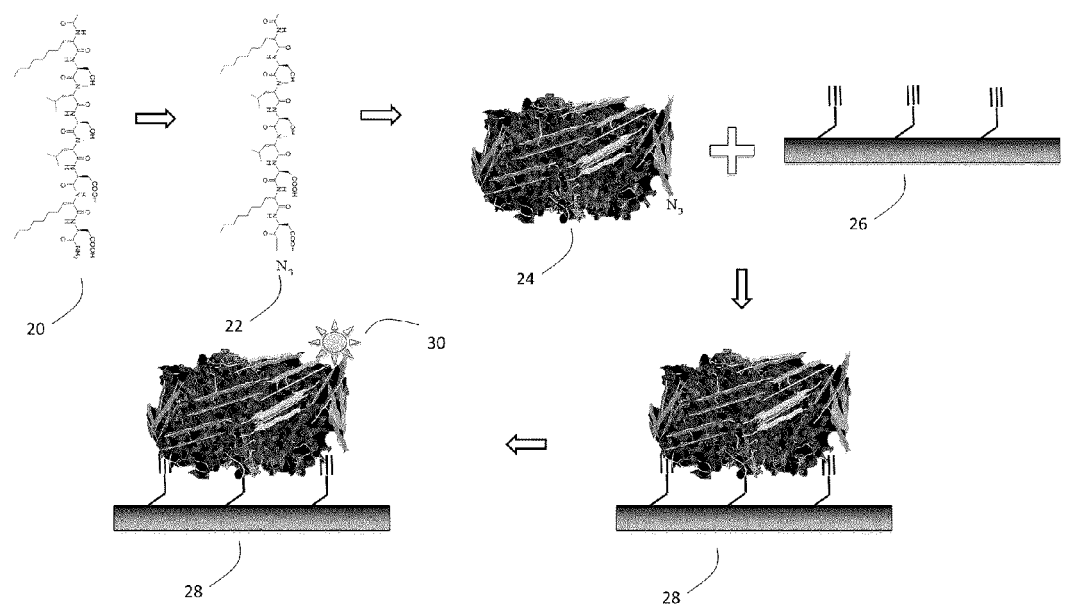
FIG. 2A shows a schematic representation of functionalized β-sheet peptide mediated immobilization of an exemplary membrane protein.

One aspect of the invention provides a complex formed by functionalized β-sheet peptides (FBPs) and a membrane protein (MP). Once the functionalized β-sheet peptides form a stable complex with the membrane protein, the functional group on the functionalized β-sheet peptides will allow the FBP:MP complex to be immobilized on a solid support. For example, as illustrated in FIG. 2A, a β-sheet peptide 20 is functionalized via peptide modification (e.g. with an azide functional group, $N_3$ added at the C-terminal end of the peptide as illustrated) to provide a functionalized β-sheet peptide 22. The functionalized β-sheet peptide 22 is combined with a membrane protein (illustrated as a ribbon diagram) and is believed to assemble, without being bound by theory, as a β-sheet barrel on the hydrophobic outer surface of the membrane protein to provide a functionalized β-sheet peptide-membrane protein (FBP:MP) complex 24. The azide-FBP:MP complex 24 is then immobilized on a solid support pre-functionalized with an alkyne end group 26. Covalent bond formation between the azide and alkyne group covalently immobilizes the FBP:MP on the solid support surface to provide an immobilized FBP:MP complex 28. In some embodiments, further studies can be carried out, for example binding characterization using a fluorescent labeled substrate or antibody 30.

Figure 2B:
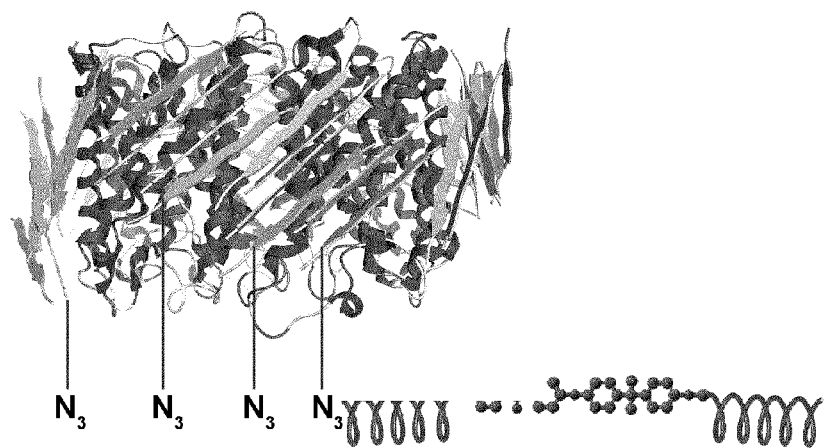
FIG. 2B shows a schematic representation of functionalized β-sheet peptide mediated conjugation of AqpZ to a polymer.

As indicated above, the solid support is not limited to an alkyne-functionalized solid support 26 and could be any suitable polymer surface, such as a polymer chain cast in a membrane, an inorganic surface, such as gold surface, some other solid state surface, or any other suitable support. As shown in FIG. 2B, in some embodiments, the functionalized β-sheet peptide-stabilized membrane protein can be conjugated to a polymer chain cast in a membrane.

Figure 2C:
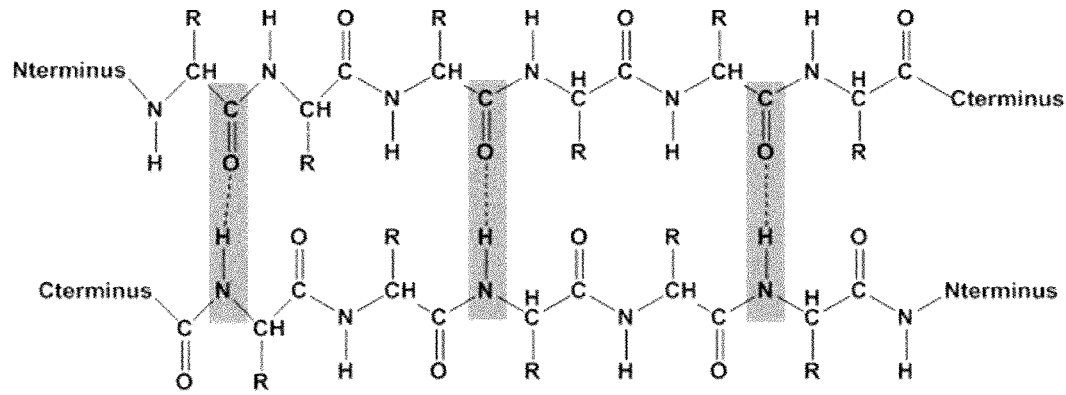
FIG. 2C shows schematically a proposed organization of β-sheet peptides when stabilizing membrane proteins.

FIG. 2C shows schematically how the functionalized β-sheet peptides may interact to form a β-sheet structure to stabilize the membrane proteins. Without being bound by theory, it is believed that the hydrophobic residues of the alternating hydrophobic-hydrophilic peptide sequence interact with the hydrophobic regions of the transmembrane proteins. Thus, the membrane proteins are stabilized by and form a stable complex with the functionalized β-sheet peptides. The resulting complex can be covalently anchored to a suitable support by reacting the functional group of the functionalized β-sheet peptide with a suitable functional group on the support.

In some embodiments, the functionalized β-sheet peptides comprise custom sequences. For example, individual amino acids within the peptide may have different functional groups which can be used to tune the physiochemical behaviors of the FBP:MP complex. These functional groups may be used to crosslink the FBP:MP complexes to one another while maintaining functionality of the protein. This could be done to create tightly packed and highly ordered protein arrays, in one example embodiment, or using long linker molecules to achieve a loose mesh-type structure in a further example embodiment. For example, in one example embodiment, a vinyl functional group is introduced within the peptide sequence to generate a vinyl functionalized β-sheet peptide. In one example embodiment, the vinyl functionalized β-sheet peptide has the structure (8) shown below. After the formation of a membrane-protein:vinyl-BP1 complex, the vinyl functionality on the functionalized β-sheet peptide can be activated to undergo crosslinking. This leads to the formation of a protein complex that is crosslinked by the vinyl functionality.

In one example embodiment, the functionalized β-sheet peptide comprises the sequence acetyloctyl)Gly-Ser-Leu-Ser-Leu-Asp-(octyl)Gly-Asp-$NH_2$ (SEQ ID NO:1) having the general structure (2) and bearing any suitable functional group.

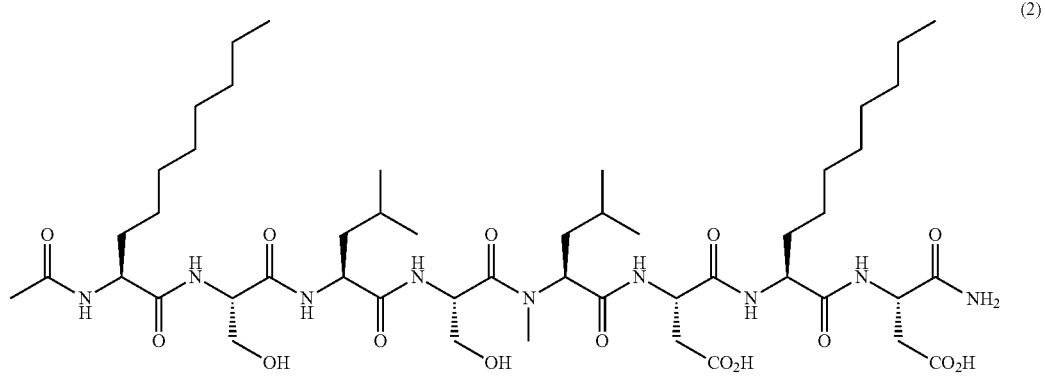 [SMILES: CCCCCCCC[C@H](NC(C)=O)C(=O)N[C@@H](CO)C(=O)N[C@@H](CC(C)C)C(=O)N[C@@H](CO)C(=O)N(C)[C@@H](CC(C)C)C(=O)N[C@@H](CC(=O)O)C(=O)N[C@@H](CCCCCCCC)C(=O)N[C@@H](CC(=O)O)C(N)=O]

(2)

In alternative example embodiments, the functionalized β-sheet peptide could have any suitable sequence having alternating polar and apolar residues and a hydrophobic moiety at each end. The N-methyl amino acids of structure (2), which is provided on the second leucine in the illustrated embodiment, could be placed in different locations, combined in any desired number, or omitted in alternative embodiments. In some embodiments, the amino acid used at a particular location could be substituted by a different naturally-occurring amino acid or a modified amino acid that has similar properties. For example, in some embodiments, the functionalized β-sheet peptide could have a sequence comprising any one of the amino acids listed in column 1 of Table 1 below at the first position, any one of the amino acids listed in column 2 of Table 1 below at the second position, and so on, to provide a β-sheet peptide having alternating polar and apolar residues and a hydrophobic moiety at or near each end of the peptide. In some embodiments, additional amino acids could be present at either the C-terminal or N-terminal end of the β-sheet peptide. For example, in some embodiments, additional amino acids could be provided at either or both of the C-terminal or N-terminal ends of the β-sheet peptide and the sequence of such additional amino acids could be selected to form a certain secondary structure that does not interfere with stabilization of the membrane protein by the functionalized β-sheet peptide, and/or the sequence could be selected to contain specific functional groups, e.g. to facilitate cross-linking or surface attachment of the membrane proteins stabilized by the functionalized β-sheet peptide.

TABLE 1

Potential amino acid sequences for construction of functionalized β-sheet peptides.

| Position 1 | Position 2 | Position 3 | Position 4 | Position 5 | Position 6 | Position 7 | Position 8 |
|---|---|---|---|---|---|---|---|
| octyl(Gly) | Ser | Leu | Ser | Leu | Asp | octyl(Gly) | Asp |
| octyl(Ala) | Thr | Ile | Thr | Ile | Asn | octyl(Ala) | Asn |
|  | Cys | Val | Cys | Val | Glu |  | Glu |
|  |  |  |  |  | Gln |  | Gln |
|  |  |  |  |  | His |  | His |

In some embodiments, a functional group is provided on the functionalized β-sheet peptide by replacing one of the amino acids in the sequence listed in Table 1 with a different amino acid that can be more easily functionalized, e.g. replacing Ser at position 2 with a Cys, or e.g. replacing Ser at position 4 with a Cys, since Cys contains a free thiol group which can be easily modified.

In some embodiments, a functional group is provided on the functionalized β-sheet peptide by incorporating a modified amino acid residue bearing a suitable functional group in the to polypeptide during synthesis. Table 2 shows how the sequence of the functionalized β-sheet peptide could be modified using modified amino acids in some example embodiments. The exemplary modified amino acids shown in Table 2 are illustrative in nature only, and it will be clear to those skilled in the art that other modified amino acids could be used instead.

TABLE 2

Exemplary potential modified amino acid sequences for construction of functionalized β-sheet peptides.

| Pos. 1 | Position 2 | Pos. 3 | Position 4 | Pos. 5 | Position 6 | Pos. 7 | Position 8 |
|---|---|---|---|---|---|---|---|
|  | Propargylglycine |  | Propargylglycine |  | Propargylglycine |  | Propargylglycine |
|  | Allylglycine |  | Allylglycine |  | Allylglycine |  | Allylglycine |
|  | Azido-pentanoic acid |  | Azido-pentanoic acid |  | Azido-pentanoic acid |  | Azido-pentanoic acid |
|  | Azidopentyl alanine |  | Azidopentyl alanine |  | Azidopentyl alanine |  | Azidopentyl alanine |

In some embodiments, sequence substitutions, including those example sequence substitutions described above, are achieved by replacing an amino acid monomer of a peptide having, for example, the structure (2), (3) or (4) with the desired amino acid monomer during the synthesis, since the same reaction chemistry applies to the various different amino acids (i.e. a peptide bond is formed between the amine of the peptide and the carboxylate group of the incoming amino acid monomer during peptide synthesis, for example using a conventional solid phase peptide synthesizer). In some embodiments, the choice of amino acid to be modified is rationalized so that the functionalized amino acid is in a position that is solvent exposed. In some embodiments, the functionalized amino acid is provided at position 2, position 4, position 6 or position 8 of the exemplary potential amino acid sequences listed in Table 1. In alternative embodiments, more than one functional amino acid could be provided within the peptide sequence.

In some embodiments, a modified or non-naturally occurring amino acid is added at either or both of the N-terminus or the C-terminus of the peptide. In such embodiments, the functionalized β-sheet peptide has a sequence that is longer than eight amino acids, for example nine amino acids or ten amino acids. For example, in one example embodiment, a propargyl glycine (commercially available) is added to the C-terminus of a β-sheet peptide having the BP1 sequence via conventional peptide synthesis methods to make a 9 amino-acid sequence having the structure (5) with the peptide sequence acetykoctyl)Gly-Ser-Leu-Ser-Leu-Asp-(octyl)Gly-Asp-(propargyl)Gly-NH$_2$ (SEQ ID NO:12). The N-methyl amino acid of structure (5) is provided on the second leucine within the sequence, but could be provided on any desired amino acid residue or omitted in alternative embodiments. In alternative embodiments, more than one N-methyl amino acid could be present.

glycine derivatives and other modified amino acids such as allylglycine, cyclopropylglycine, azido-pentanoic amino acid, and the like could be incorporated using the same strategy.

In some embodiments, a modified or non-naturally occurring amino acid is inserted within the peptide sequence. In some such embodiments, the modified or non-naturally occurring amino acid is propargyl glycine, allylglycine, cyclopropylglycine, azido-pentanoic amino acid, or the like. Other amino acids besides glycine could be modified and inserted into the peptide in alternative embodiments. In some such embodiments, one or more additional amino acids may be added to either or both of the N-terminus or the C-terminus of the peptide. In some such embodiments, the one or more additional amino acids is added to maintain the alternating polar residue—non-polar residue sequence of the peptide. In such embodiments, the functionalized β-sheet peptide has a sequence that is longer than eight amino acids, for example ten amino acids, due to the insertion of at least two additional amino acids into the peptide sequence.

In another example embodiment, the β-sheet peptide comprises an azide end-functionalized β-sheet peptide. In one such example embodiment, the β-sheet peptide comprises an azide end-functionalized β-sheet peptide having the structure (6). Structure (6) has the general peptide sequence acetyl-azidohomoalanine-(octyl)Gly-Ser-Leu-Ser-Leu-Asp-(octyl)Gly-Asp-NH$_2$ (SEQ ID NO:13). Structure (6) comprises nine amino acids. The N-terminal amino acid of structure (6) is an exemplary modified amino acid, azidohomoalanine, which the inventors synthesized according to reported procedures. In structure (6), the N-methyl group is provided on the second leucine. In alternative embodiments, additional N-methyl groups could be pro-

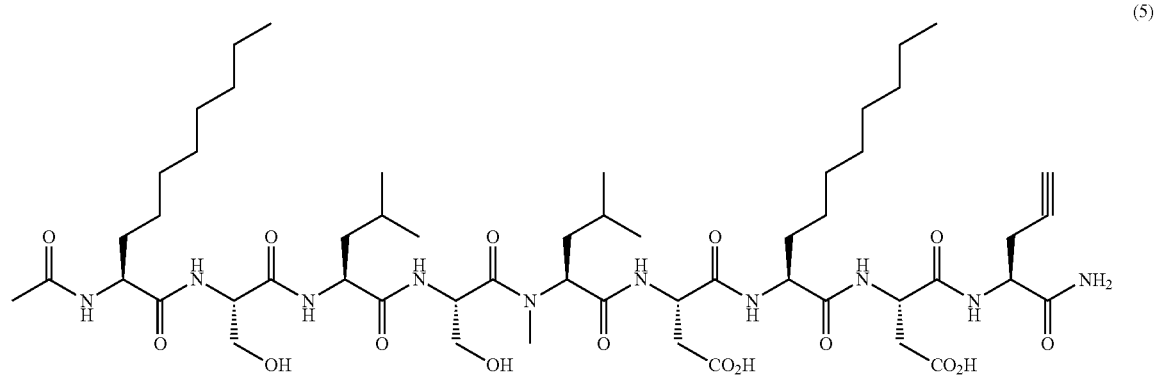 [SMILES: C#CC[C@H](NC(=O)[C@H](CC(=O)O)NC(=O)[C@H](CCCCCCCC)NC(=O)[C@H](CC(=O)O)NC(=O)[C@H](CC(C)C)N(C)C(=O)[C@H](CO)NC(=O)[C@H](CC(C)C)NC(=O)[C@H](CO)NC(=O)[C@H](CCCCCCCC)NC(C)=O)C(N)=O]

(5)

Figure 4A:
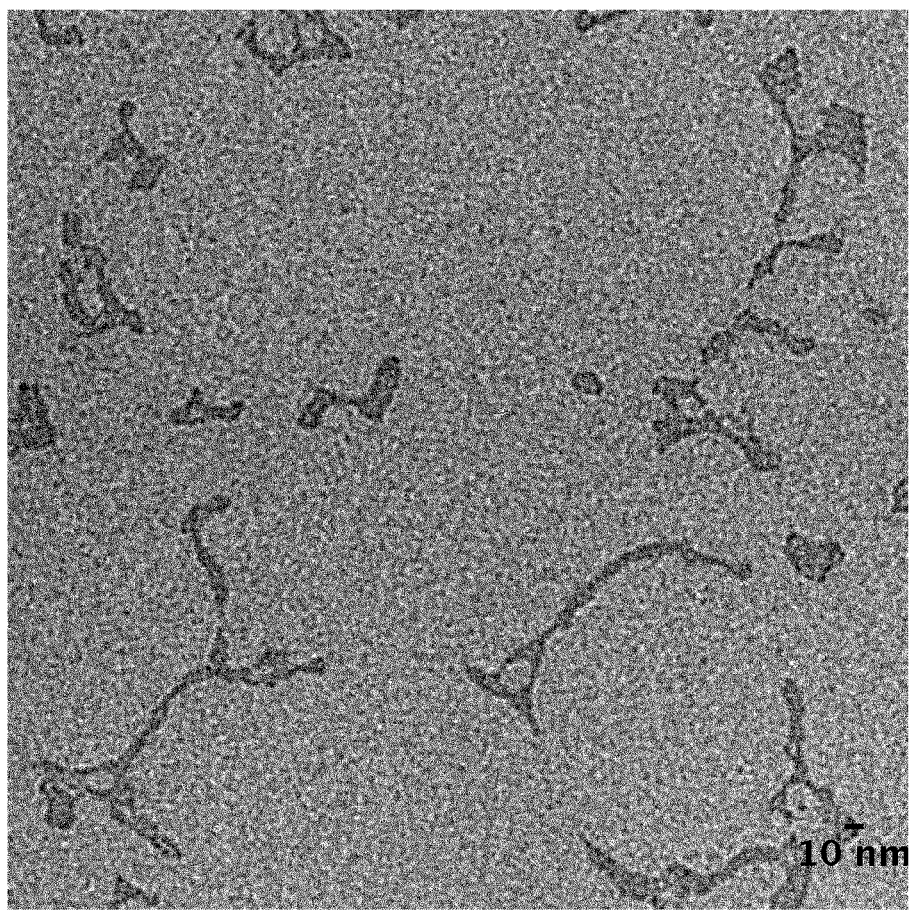
FIGS. 4A and 4B show the characterization of a functionalized β-sheet peptide with an alkyne functional group at the C-terminus of the peptide.

The resulting sequence has a propargyl functionality and can assemble into fibril structure as shown in FIG. 4A, which is an indication of beta-sheet formation. Similarly, vided within the peptide, or the N-methyl group(s) could be provided on amino acids other than the second leucine, or the N-methyl groups could be omitted altogether.

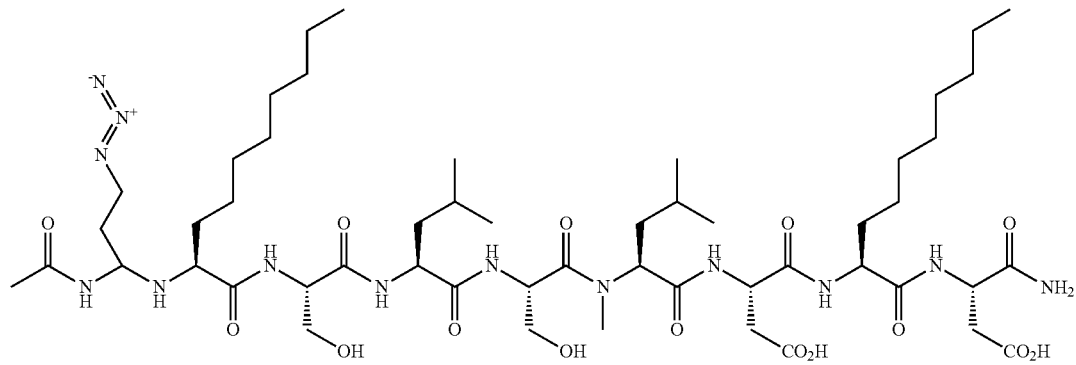

(6)

In another example embodiment, the β-sheet peptide comprises an alkyne end-functionalized β-sheet peptide. In one such example embodiment, the β-sheet peptide comprises an alkyne end-functionalized β-sheet peptide having the structure (7), wherein the alkyne end functionality is provided at the N-terminus of the peptide. Structure (7) has the general peptide sequence acetyl-(propargyl)Gly-(octyl)Gly-Ser-Leu-Ser-Leu-Asp-(octyl)Gly-Asp-NH$_2$ (SEQ ID NO:14). Structure (7) comprises nine amino acids. In structure (7), the N-methyl group is provided on the second leucine. In alternative embodiments, additional N-methyl groups could be provided within the peptide, or the N-methyl group(s) could be provided on amino acids other than the second leucine, or the N-methyl groups could be omitted altogether.

In another example embodiment, the β-sheet peptide comprises an alkene mid-functionalized β-sheet peptide. In one such example embodiment, the β-sheet peptide comprises an alkene mid-functionalized β-sheet peptide having the structure (8). Structure (8) has the general peptide sequence acetyl-(octyl)Gly-Ser-Leu-Ser-amino hexenoic acid-Leu-Asp-(octyl)Gly-Asp-Gly-Leu-NH$_2$ (SEQ ID NO:15). Structure (8) comprises 11 amino acids. In structure (8), the N-methyl group is provided on the second leucine. In alternative embodiments, additional N-methyl groups could be provided within the peptide, or the N-methyl group(s) could be provided on amino acids other than the second leucine, or the N-methyl groups could be omitted altogether.

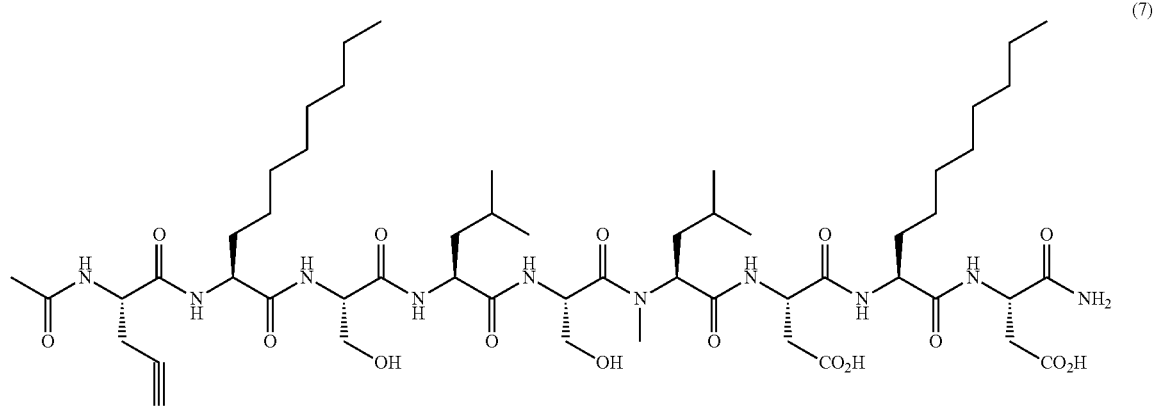 [SMILES: C#CC[C@H](NC(C)=O)C(=O)N[C@@H](CCCCCCCC)C(=O)N[C@@H](CO)C(=O)N[C@@H](CC(C)C)C(=O)N[C@@H](CO)C(=O)N(C)[C@@H](CC(C)C)C(=O)N[C@@H](CC(=O)O)C(=O)N[C@@H](CCCCCCCC)C(=O)N[C@@H](CC(=O)O)C(N)=O]

(7)

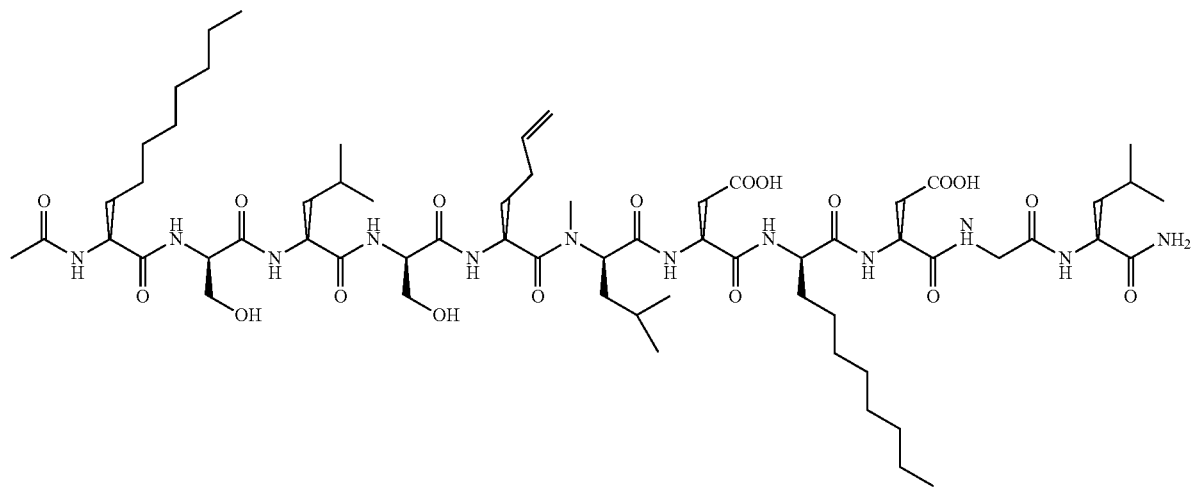

(8)

In alternative embodiments, an alkyne mid-functionalized β-sheet peptide is provided by substituting the vinyl-modified amino acid used to provide the alkene mid-functionalized β-sheet peptide with a corresponding propargyl-modified amino acid. Thus, any suitable functional group can be positioned at any desired location within the functionalized β-sheet peptide by incorporating the correspondingly modified amino acid at the desired location within the peptide sequence.

In some embodiments, the β-sheet peptide is functionalized after it has been synthesized to by any suitable chemical reaction. For example in some embodiments, the β-sheet peptide could be functionalized so that it will form covalent bonds via its amine and/or carboxyl groups. In one such example embodiment, the free amine group in the β-sheet peptide is reacted with M-phenylene-diamine (MPD) and trimesoyl chloride (TMC) to provide an amide functional group. The amide functional group can react with the backbone carbonyl groups to covalently couple the β-sheet peptides together. In another such example embodiment, the free carboxyl group of the β-sheet peptide can react with M-phenylene-diamine (MPD) to form an amide functional group that can similarly form a covalent linkage with the carbonyl groups of the peptide backbone to covalently join the β-sheet peptides together. In one such embodiment, the covalently linked β-sheet peptide-membrane protein complex forms an interfacial polymer layer that can be coupled to a membrane, for example a polysulfone membrane to form a polyamide-polysulfone interfacial composite membrane, via hydrogen bonding interactions (see e.g. Ghosh et al., 2009). The hydrogen bonding interactions between the polyamide and polysulfone layers of the composite membrane can be modulated, for example by adding a pore forming agent such as polyvinylpyrolidone (PVP) during casting of the membrane or adjusting the surface roughness of the polysulfone membrane, and other factors such as adsorption of the polyamide layer to pores on the polysulfone or the like can also enhance the interaction between the two layers of the composite membrane.

In some embodiments, the functionalized β-sheet peptide bears a functional group at any suitable location. In some embodiments, the functional group is a crosslinking functional group. In some embodiments, the crosslinking functional group is an azide, alkyne, alkene, thio, azidophenyl, vinyl, or the like.

In some embodiments, the functional group is provided at the N-terminus of the peptide. For example, in one example embodiment having the core β-sheet peptide structure (2), the functional group is provided on the acetyl group of the peptide, such that the peptide has the general structure (9):

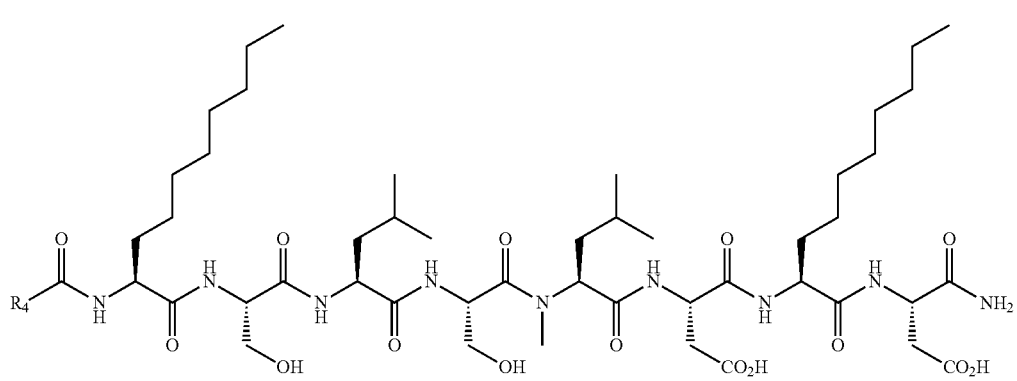

(9)

wherein $R_4$ can be any suitable functional group, including for example an azide group, alkyne group, alkene group, thio group, azidophenyl group, vinyl group, or the like.

In some embodiments, the functional group is provided at the C-terminus of the peptide. For example, in one example embodiment having the core β-sheet peptide structure (2), the functional group is provided on the amino group of the peptide, such that the peptide has the general structure (10):

peptides with NHS-Diazirine (SDA) biofunctionalized crosslinker (Thermo Scientific Pierce) will generate functionalized β-sheet peptides with a photo-reactive diazirine functional group at the N-terminus. After complex formation with the membrane protein of interest, the diazirine-FBP: MP can be crosslinked to a solid support through the diazirine functionality. Furthermore, as the functional group in this specific example (i.e., diazirine functional group) is

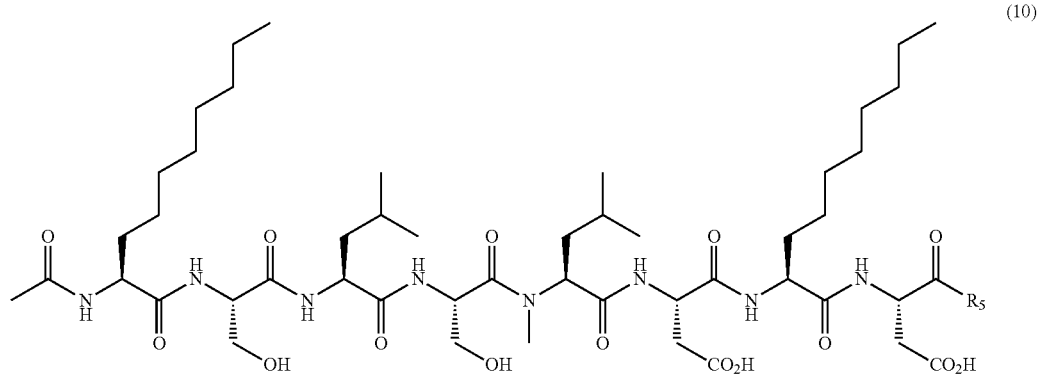

(10)

wherein $R_5$ can be any suitable functional group, including for example an azide group, alkyne group, alkene group, thio group, azidophenyl group, vinyl group, or the like.

In addition to functionalizing β-sheet peptides by incorporating side chains with particular functionality during peptide synthesis, β-sheet peptides can be functionalized by reacting them with bifunctional crosslinkers at the α-amine at the N-terminus in their deacetyl form. A variety of such bifunctional crosslinkers are commercially available or can be readily synthesized, for example sulfosuccinimidyl 6-(4'-azido-2'-nitrophenylamino)hexanoate (sulfo-NHS-SANPAH, ThermoFisher Scientific), sulfosuccinimidyl 4,4'-azipentanoate (sulfo-NHS-Diazirine, ThermoFisher Scientific), succinimidyl 2-((4,4'-azipentanamido)ethyl)-1,3'-dithiopropionate (NHS-SS-Diazirine, ThermoFisher Scientific), and the like. For example, reacting deacetyl β-sheet photo-reactive, the diazirine-FBP:MP may be immobilized in desired patterns through a photo-mask.

Reacting a deacetyl β-sheet peptide (which has the sequence of BP1 in one example embodiment) with N-5-azido-2-nitrobenzoyloxysuccinimide (ANB-NOS) (Thermo Scientific Pierce) will result in an ANB-modified β-sheet peptide (e.g. ANB-BP1 as shown in Scheme 1), which has a photo-reactive aryl-azide functional group at the N-terminus. After complex formation with the membrane protein of interest, the ANB-BP:MP can be crosslinked to a solid support through the aryl-azide functionality. Furthermore, as the functional group in this specific example (i.e. ANB) is photo-reactive, the ANB-BP:MP complex can be immobilized in any desired pattern through a photo-mask.

Scheme 1. Reaction scheme of non-acetyl BP1 with ANB-NOS to generate a photoactivable functionalized β-sheet peptide (FBP1).

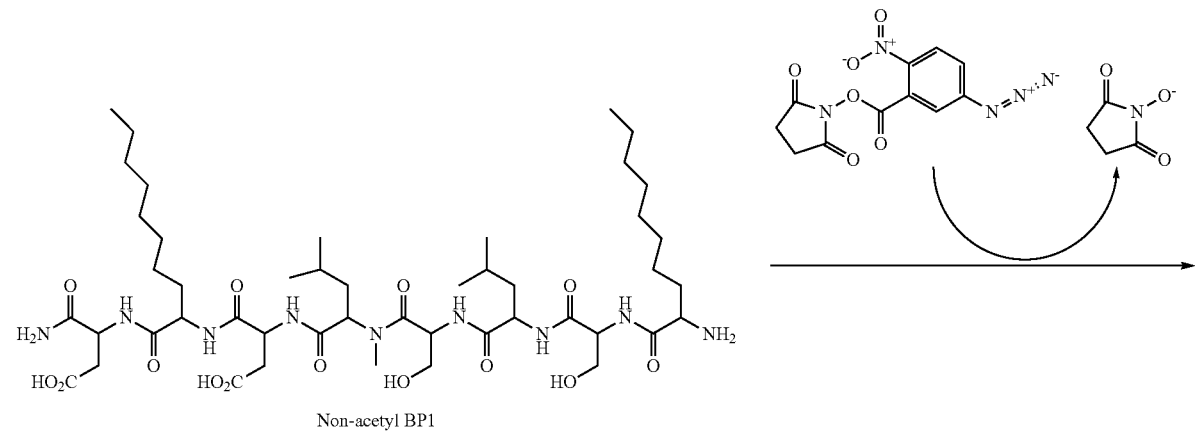

Non-acetyl BP1

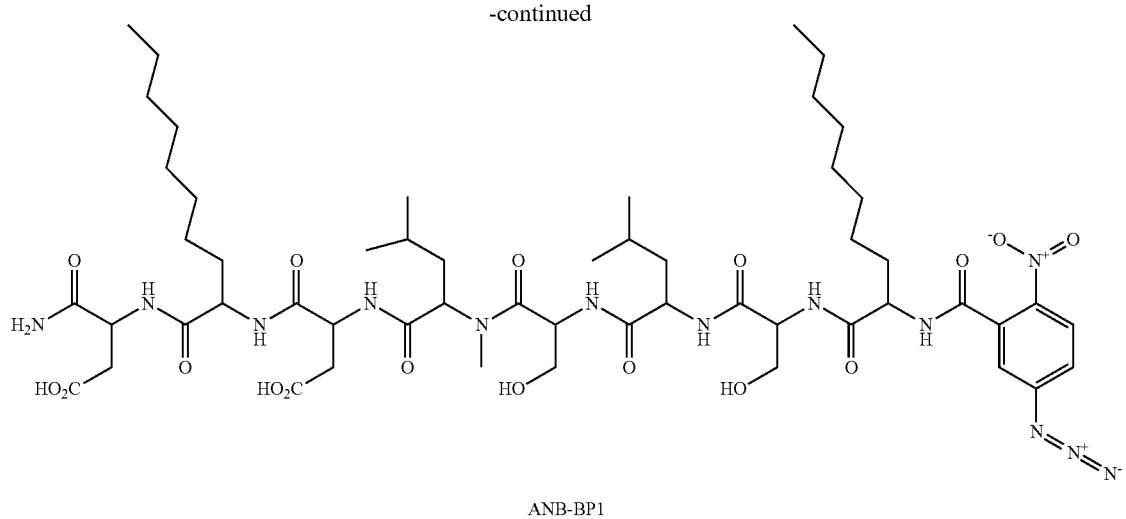

ANB-BP1

In one embodiment, the aforementioned functionalized β-sheet peptides and FBP:MP complexes are used to create compartmentalized reactors based upon arrays of membrane proteins with specific functionality, namely aquaporins, to purify water.

In one embodiment, the aforementioned functionalized β-sheet peptides and FBP:MP complexes are useful in membrane-based filters. Such filters may be used for water desalination (e.g., using FBP:aquaporin complexes), or for controlled separation of specialty chemicals, or may be active controlled filters/valving using pH and/or pressure.

In some embodiments, using aquaporin stabilized by functionalized β-sheet peptides provides the possibility of surface immobilization, allowing the construction of novel membranes for water purification applications.

The matrix or support on which the functionalized β-sheet peptide stabilized aquaporin is immobilized should be selected to be compatible with and facilitate proper functioning of the immobilized peptide-protein complexes. In some embodiments, the matrix on which the functionalized β-sheet peptide stabilized aquaporin is immobilized is a modified polymer (for example, a polysulfone, polycarbonate, polylactone, or the like). In some embodiments, the matrix on which the functionalized β-sheet peptide stabilized aquaporin is immobilized is a carbon nanotube mesh, or a composite of a carbon nanotube mesh. In some embodiments, the matrix on which the functionalized β-sheet peptide stabilized aquaporin is immobilized is nanocrystalline cellulose, or a composite of nanocrystalline cellulose.

In one example embodiment, the matrix on which the functionalized β-sheet peptide stabilized aquaporin is immobilized is a polymer. In one such example embodiment, the polymer is a polusulfone. Polysulfone is well-known in the membrane industry due to its chemical compatibility and durability, and it is a good candidate for structural modification. Polysulfone is initially functionalized to form an azide group, and is then cast into a membrane with a specific ratio of native polysulfone. The casting is performed using a liquid-induced phase inversion technique. In some embodiments, a pore developing agent is added during the casting process to form membranes with pores of a controlled size. In some embodiments, the pore developing agent is polyvinylpyrrolidone (PVP), polyethylene glycol (PEG), poly(N,N-dimethylaminoethyl methacrylate (PD-MAEMA), or the like. Any suitable pore forming agent could be used. In some embodiments, the pores have size in the range of about 5 nm to several μm in diameter, e.g. 10 μm, including any value therebetween. In some embodiments, the pores formed have a size between about 20 nm and about 200 nm in diameter, including any value therebetween, e.g. 30, 40, 50, 60, 70, 80, 90, 100, 110, 120, 130, 140, 150, 160, 170, 180 or 190 nm in diameter.

In such embodiments, the azide functionality around the pores provides the starting point for the specific attachment of functionalized β-sheet peptide stabilized aquaporin. In some such embodiments, the azide functionality around the pores provides the starting point for attachment of a propargyl-modified functionalized β-sheet peptide that is used to stabilize an aquaporin molecule. Thus, the aquaporin-functionalized-β-sheet peptide complex can be covalently cross-linked via the functionalized β-sheet peptide to the polysulfone substrate through mild click chemistry resulting in a robust and scalable protein-loaded biomimetic reverse osmosis membrane.

In one example embodiment incorporating pores, after the functionalized β-sheet peptide-stabilized aquaporin has been cross-linked to the polysulfone substrate, inter-facial polymerization is carried out to minimize any leakage of water (or water carrying one or more contaminants) through the pores in the membrane.

In one example embodiment, a PSU—$CH_2N_3$ solution used to prepare an azide-functionalized polysulfone membrane is prepared following the general reaction set forth in Scheme 2, for example as described in Evram et al.

Scheme 2. Preparation of solution for making azide functionalized polysulfone membrane.

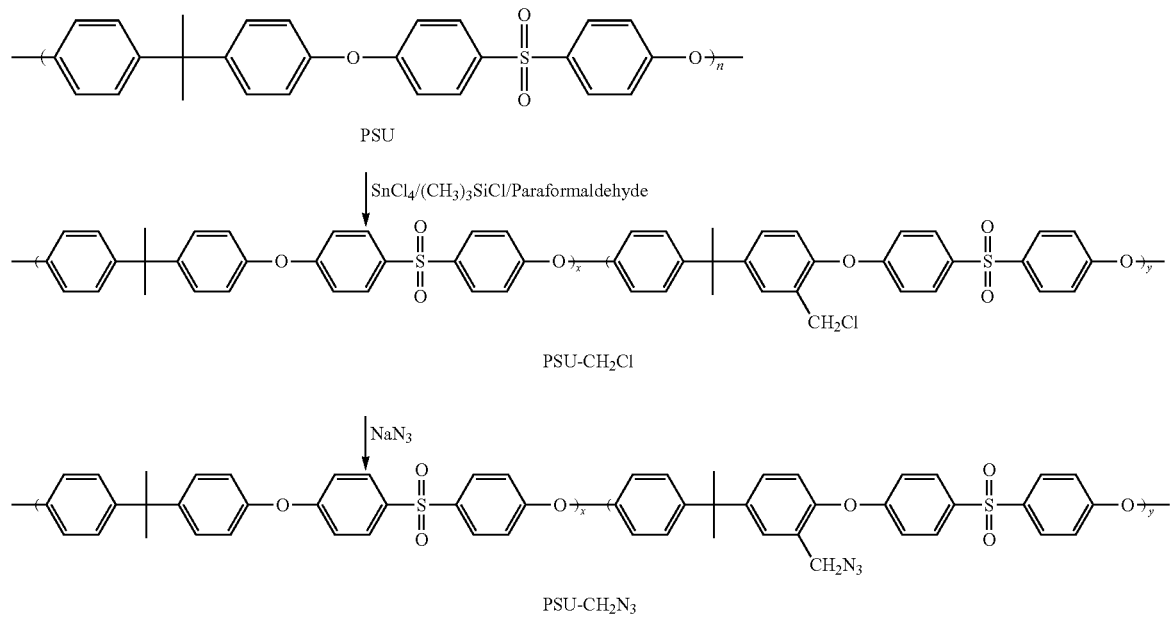

Figure 3:
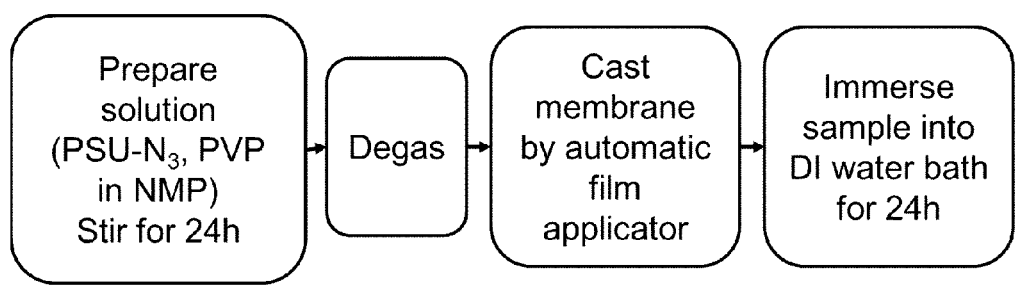
FIG. 3 shows an example embodiment of a process for making a polysulfone membrane bearing aquaporin tethered by functionalized β-sheet peptides.

Following preparation of the PSU-CH$_2$N$_3$ solution, the polysulfone membrane is prepared according to the general method illustrated in FIG. 3. The PSU-CH$_2$N$_3$ is combined with a suitable pore forming agent (e.g. PVP in the illustrated embodiment) in a suitable solvent (e.g. N-methyl-2-pyrrolidone, NMP) in the illustrated embodiment and stirred for a suitable period (e.g. 24 hours in the illustrated embodiment). The solution is degassed, cast as a membrane in any suitable manner (e.g. by an automatic film applicator in the illustrated embodiment), and rinsed to remove excess reactants (e.g. by immersing in a deionized water bath for 24 hours in the illustrated embodiment). In some embodiments, the pore forming agent is omitted.

In one example embodiment, an aquaporin molecule stabilized by a functionalized β-sheet peptide having the general structure of BP1 and bearing a propargyl functional group (i.e. having structure (5)) is coupled to the azide functionalized polysulfone membrane by click chemistry, as illustrated in Scheme 3. It is within the expected ability of the person of ordinary skill in the art to carry out such a reaction using click chemistry. In one example conducted by the inventors, the click chemistry between the polysulfone membrane and the functionalized β-peptide was carried out using copper sulfate (CuSO$_4$.5H$_2$O) and sodium ascorbate. A 1:3 equivalent of this catalyst is mixed with 13 equivalents of propargyl-functionalized β-sheet peptide in methylene chloride solvent. The mixture was stirred at room temperature for 12 hours under argon atmosphere. The product was recovered by solvent evaporation.

Scheme 3. Reaction of propargyl-functionalized β-sheet peptide with azide functionalized polysulfone membrane.

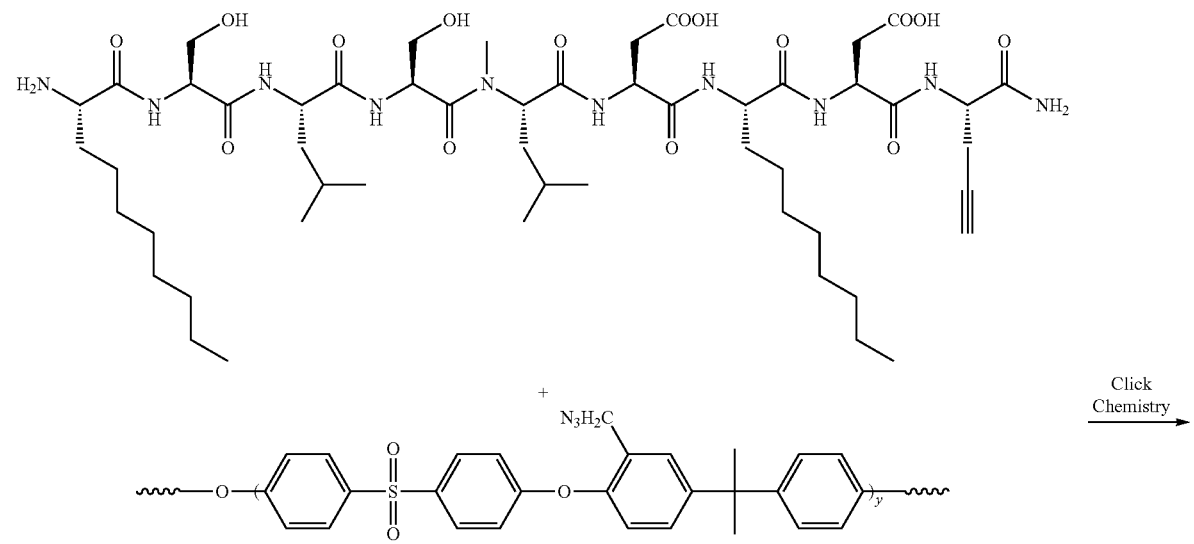

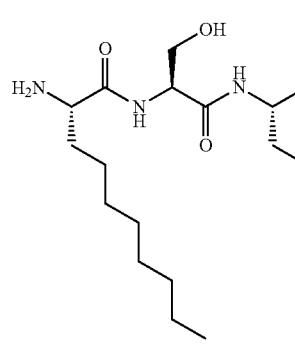
-continued
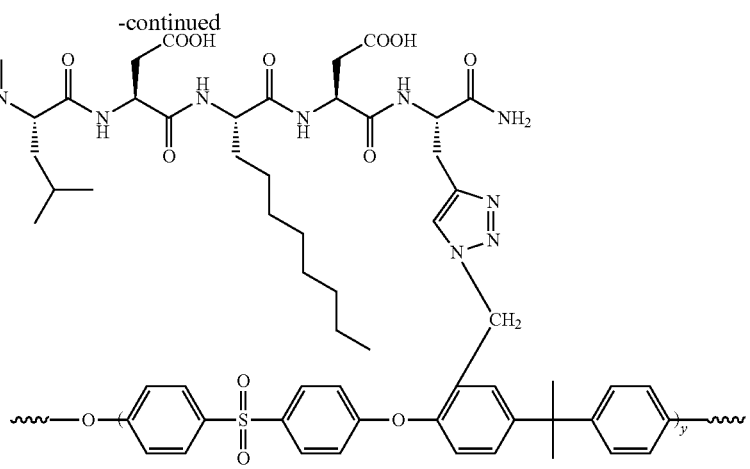

In one example embodiment, the matrix on which the functionalized β-sheet peptide stabilized aquaporin is immobilized is carbon nanotube (CNT) mesh. Native carbon nanotubes are hydrophobic in nature and can assemble into a membrane by forming a mesh by themselves or with a composite, or can be assembled by appropriate crosslinking. In order to utilize carbon nanotube mesh as a substrate for protein incorporation, surface chemistry is first carried out to facilitate conjugation reactions. In one example embodiment, oxidation is carried out by acidolysis or plasmoxidation to provide a free carboxy group on the surface of the carbon nanotube mesh, which can be reacted with amines possessing -ene groups to facilitate UV crosslinking to the carbon nanotube matrix. This strategy will provide vinyl functionalization on the carbon nanotube mesh to facilitate UV crosslinking with various functional groups.

Crosslinking of the carbon nanotube mesh with functionalized β-sheet peptide stabilized aquaporin can be achieved by using a functionalized β-sheet peptide bearing a vinyl functional group using an appropriate UV irradiation. For example, in some embodiments, a functionalized β-sheet peptide having the structure (8) could be used. In some embodiments, the UV irradiation used has a wavelength in the range of 300 to 400 nm, or any value therebetween, e.g. 310, 320, 330, 340, 350, 360, 370, 380 or 390 nm. In some embodiments, after the functionalized β-sheet peptide stabilized aquaporin has been coupled to the carbon nanotube mesh, the mesh can be densified by tightly packing the carbon nanotube fibers to avoid any water leakage around the aquaporin. In some such embodiments, densification could be carried out by soaking the construct in methanol and vacuum drying, taking care that the conditions used to not disrupt the functionality of the stabilized aquaporin molecules.

In one example embodiment, the matrix on which the functionalized β-sheet peptide stabilized aquaporin is immobilized is nanocrystalline cellulose. Similarly to the use of carbon nanotubes as a matrix, surface activation of the nanocrystalline cellulose substrate, which has abundant hydroxyl groups on the surface, can be performed using established techniques, such as a Fisher Esterification to introduce carboxylate functional group, followed by an amine-ene biofunctional linker to provide a surface with vinyl functional group (see e.g.: Habibi, Y. (2014)). The vinyl functional group can be further reacted with appropriate functional groups provided on the functionalized β-sheet peptides using established chemical techniques.

Preparing membranes according to some embodiments by utilizing surface functionality of the membranes and carrying out protein stabilization using β-sheet peptides bearing certain modifications can enable the production of biomimetic membranes capable of reproducing nature's selectivity to selectively pass or move specified particles across a membrane. In some embodiments, the specified particles are ions or molecules. A membrane protein can be selected to selectively pass or transport a specified particle, which could be a desired ion, a molecule such as water, RNA, DNA, or the like. For example, any of the membrane proteins listed in Table 1 of Habel et al. (2015), which have been studied using a di-block or tri-block polymer system, could be stabilized on a membrane using functionalized β-sheet peptides and used to transport its corresponding transport cargo. Thus, alamethicin, hemolysin, NADH reductase, OmpG, OmpF or RC (photosynthetic reaction centre) could be used to transport electrons; alamethicin could be used to transport calcium or calcein; NtAPQ1 or NtPIP2:1 could be used to transport carbon dioxide, AQP0, AQP10 or SoPIP2; 1 could be used to transport water in the same way that AqpZ has been demonstrated to transport water as described in this specification; TsX could be used to transport nucleosides; OmpF could be used to transport large organic molecules such as acridine orange, paraquat, pyocyanin, actylthiocholine, enone, ELF97, 7-ADCA, PGME, nucleosides, ampicillin, L-ascorbic acid, CO, $Na_2S_2O_4$, $ONOO^-$; gramicidin A could be used to transport monovalent cations; MloK1 could be used to transport potassium; LamB could be used to transport sugars including maltohexaose, or DNA; FhuA could be used to transport larger molecules such as sulphorhodamine B, TMB (3,3',5,5'-tetramethylbenzidine), NAD, DNA, calcein; BR (bacteriorhodopsin), PR (proteorhodopsin) or BR & ATPase could be used to transport $H^+$; BR & CcO could be used to transport $H^+$ and electrons; CcO (cytochrome C oxidase) could be used to transport electrons, polymyxin B, hemolysin or cecropinA could be used to transport calcein. In some embodiments, proteins such as alpha-hemolysin, MspA (*Mycobacterium smegmatis* porin A), OmpF or OmpG could be used to transport polynucleotides, including DNA and RNA. As described in Example 3.0, the inventors have demonstrated that functionalized β-sheet peptides can be used to stabilize several membrane proteins, including AqpZ, ChIEF-mCitrine, NaChBac, $F_0F_1$-ATPase, and OmpG. ChIEF-mCitrine shares a very similar structure with BR. OmpG has very similar structure to OmpF and FhuA (i.e. all three proteins share a β-sheet barrel transmembrane domain). Thus, from the experimental data described herein and based on the structural similarities to the other membrane proteins listed above, it can be soundly predicted that the proteins listed above, and other membrane proteins including other aquaporins in addition to AqpZ, could be stabilized using functionalized β-sheet peptides and tethered to e.g. any suitable membrane construct for use in transporting or channeling the protein's corresponding transport cargo across the membrane.

Membranes incorporating functionalized β-sheet peptide stabilized aquaporins have potential application in a number of different environments. For example, in some embodiments, membranes incorporating functionalized β-sheet peptide stabilized aquaporins can be used in applications such as waste water treatment, purification of water in the oil and gas sector, desalination of water (e.g. to provide drinking water from salt water sources), as well as applications in the biotechnology and food and beverage sectors, for example removal of bacteria or whey concentration in the dairy industry, clarification and concentration of fruit and vegetable juices, use to produce starch and sweeteners, as well as process water reclamation in all industries.

In some embodiments, a membrane incorporating a functionalized β-sheet stabilized aquaporin blocks or impedes the passage of sodium ions, chloride ions, ammonia, urea, dye, pesticides, pharmaceutical waste, or other organic compounds through the membrane, while selectively allowing water to pass through the membrane.

In some embodiments, contaminated water is treated using a membrane incorporating a functionalized β-sheet stabilized aquaporin. In some embodiments, the contaminated water is an agricultural waste stream. In some such embodiments, the membrane is used to remove one or more contaminants including ammonia, urea, pesticides, synthetic fertilizers, heavy metals (including lead, arsenic, selenium or mercury), organic contaminants derived from pharmaceutical and personal care products, or microorganisms from the waste stream. In some embodiments, the contaminated water is an industrial waste stream. In some such embodiments, the membrane is used to remove one or more contaminants including phosphates, nitrates, asbestos, polychlorinated biphenyl, mercury, lead, caustic soda or other sodium compounds, sulfur, sulfuric acid, oils or petrochemicals from the waste stream.

Some embodiments of the present invention are further described with reference to the following examples, which are intended to be illustrative and not limiting in nature.

Example 1.0—Preparation of Functionalized β-Sheet Peptides (FBPs)

Example 1.1.—Chemical Synthesis of FBPs on Solid-Phase Peptide Synthesizer

Figure 4B:
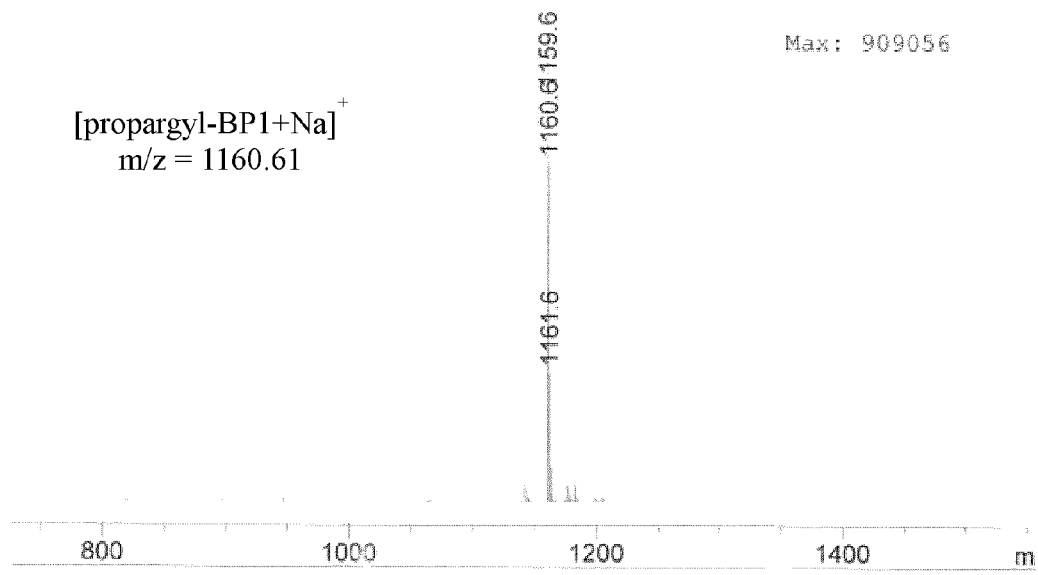

Using an amino acid with a propargyl side chain, the inventors were able to synthesize a functionalized β-sheet peptide with an alkyne functional group at the C-terminus on a solid-phase peptide synthesizer. When diluted in phosphate-buffered saline, the alkyne-FBP self-assemble into a filament structure, which indicates the alkyne-FBP retains the β-sheet-forming tendency of the β-sheet peptide. The synthesized alkyne-functionalized β-sheet peptide had the structure of BP1 but bearing a C-terminal propargylgylcine, i.e. acetyl-(octyl)Gly-Ser-Leu-Ser-Leu-Asp-(octyl)Gly-Asp-(propargyl)Gly-NH$_2$ having the structure (5) (SEQ ID NO:12). The self-assembly of the alkyne-functionalized β-sheet peptides is shown in FIG. 4A. FIG. 4B shows the mass spectrogram showing the correct molecular mass of propargyl-BP1 with high purity.

Figure 4C:
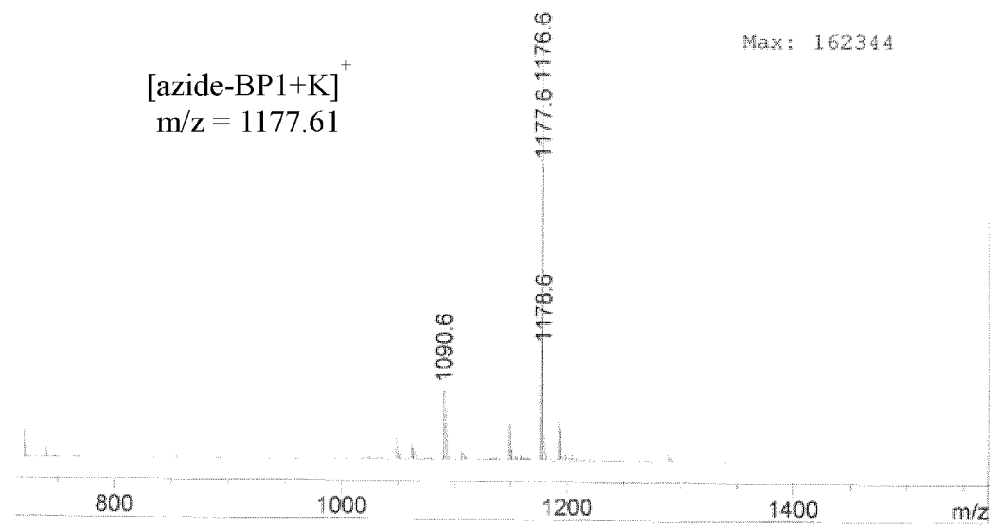
FIG. 4C shows the mass spectrogram of an azide-functionalized β-sheet peptide synthesized by the inventors.

The inventors also synthesized an azide-FBP1 having the structure (6) (SEQ ID NO:13) using a similar strategy. The mass spectrogram showing the correct molecular mass of azide-BP1 is shown in FIG. 4C.

Example 1.2—Confirmation of the Alkyne Functional Group on FBP1

Figure 5:
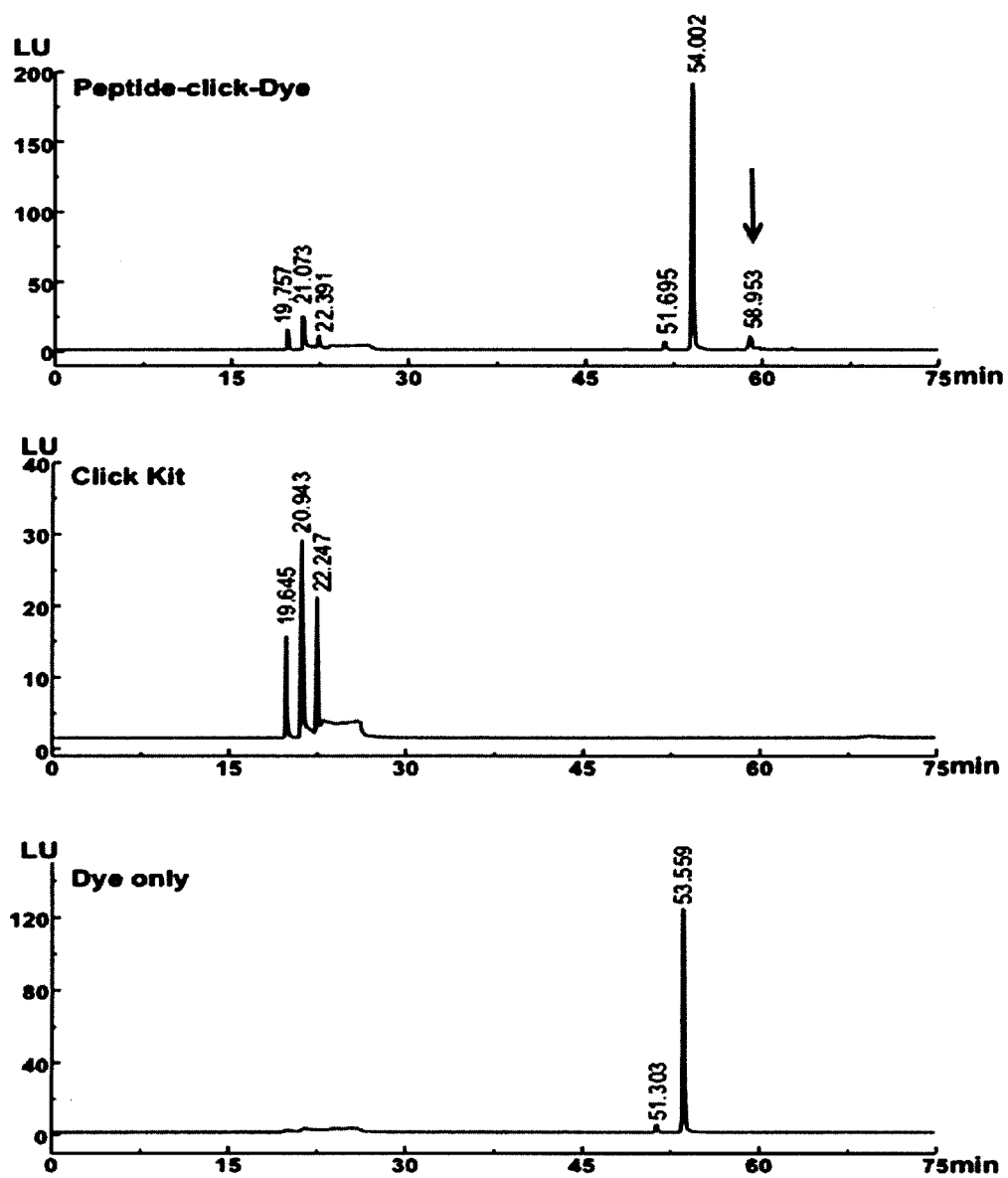
FIG. 5 shows the results of HPLC demonstrating the reaction of an alkyne group on a functionalized β-sheet peptide. The top panel shows the fluorescent HPLC elution profile of alkyne-FBP reacted with Click-iT reagents. The middle panel shows the HPLC elution profile of Click-iT buffer only. The bottom panel shows the HPLC elution profile of Click-iT dye only. The red arrow indicates the product formed in the click reaction between alkyne-FBP and Click-iT dye.

In order to confirm the presence and the active functioning of the alkyne group on the alkyne-BP1 synthesized in Example 1.1, the inventors performed reactions to click-react the alkyne group of the peptide with fluorescent tetrathyrhodamine azide (Click-iT reagent kit, Life Technology). The inventors then ran the reaction product on an HPLC equipped with a fluorescent detector. As expected, an additional fluorescent peak which did not belong to the components of the reagent kit appeared on the elution profile (indicated with an arrow in the upper panel FIG. 5; HPLC profiles for the kit alone and for the dye alone are shown in the middle and lower panels of FIG. 5, respectively). The inventors therefore can attribute this peak to the dye labeled alkyne-functionalized β-sheet peptide.

Example 2.0—Membrane Protein Purification and Formation of BP:MP Complex

The inventors have purified aquaporin (AqpZ) and verified its functionality. AqpZ is the water channel on the periplasmic membrane of *Escherichia coli*. AqpZ selectively transfers water at a high rate and based on the osmotic gradient across a cell membrane. As described above, prior attempts at using aquaporin in water purification applications have not been entirely successful. However, it is believed that a FBP:AqpZ complex according to the present disclosure will overcome at least some of the drawbacks associated with previous attempts.

Figure 6:
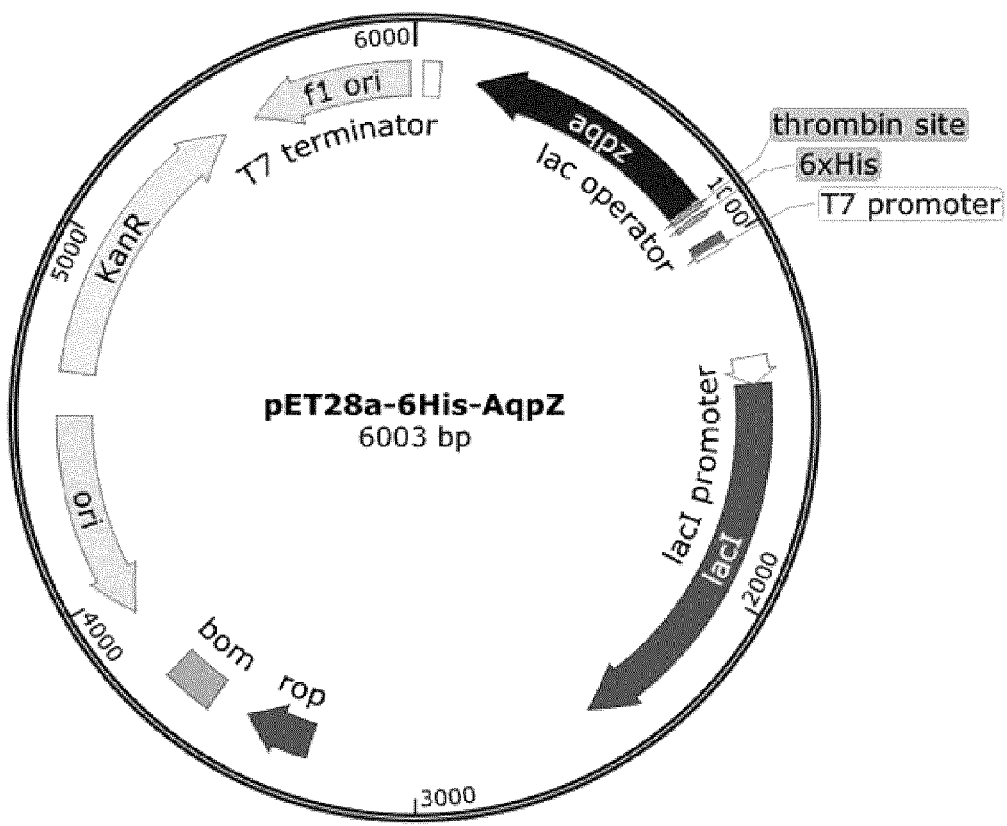
FIG. 6 shows schematically the pET28a-6His-AqpZ plasmid construct used by the inventors for expression of AqpZ in one example embodiment.

Following standard molecular biology procedures, the inventors have optimized the overexpression and purification of recombinant AqpZ in *E. coli* using n-dodecyl β-D-maltoside (DDM) as the solubilizing detergent according to previous literature[7]. Plasmid pTrc10HisAqpZ as described in reference (7) is used as a template to clone the AqpZ coding gene. One minor modification, namely codon encoding Arg3 changed from aga to cgt, was introduced to the coding gene in order to increase the translation efficiency. Codon cgt has a 10 times higher usage frequency then aga in *E. coli*. The coding gene was cloned into a commercially available plasmid (i.e. pET28a by Novagen) and the resulting plasmid construct pET28a-AqpZ was used for protein expression. Details of the plasmid can be found in FIG. 6, and the full sequence of the plasmid is provided as SEQ ID NO.: 16.

Figure 7A:
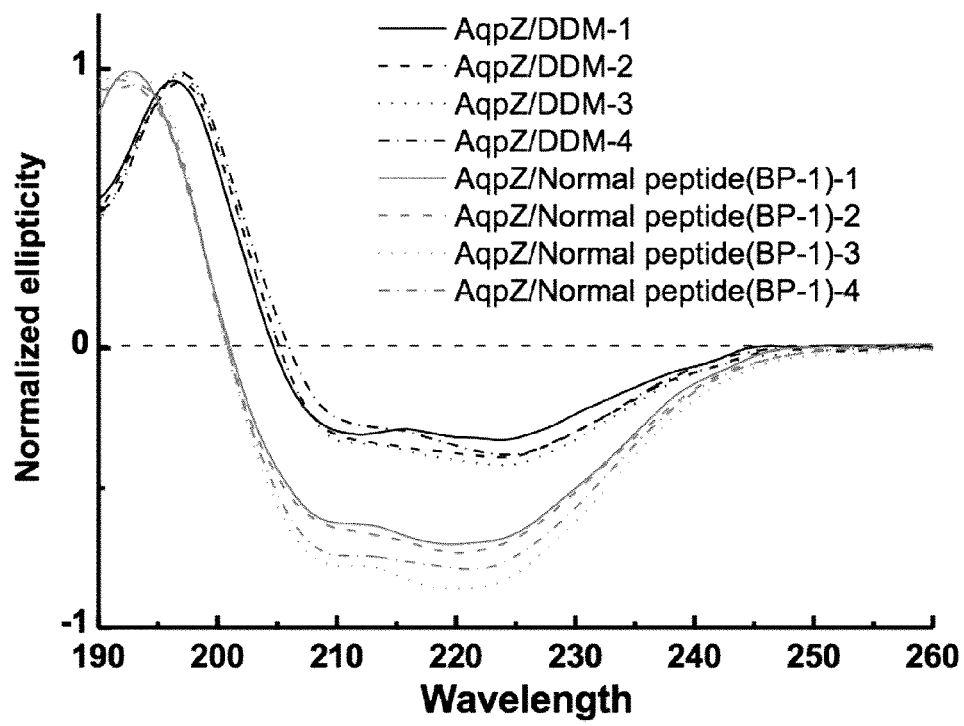
FIGS. 7A and 7B show experiments demonstrating the complex formation of BP1:AqpZ and its stability.
Figure 7B:
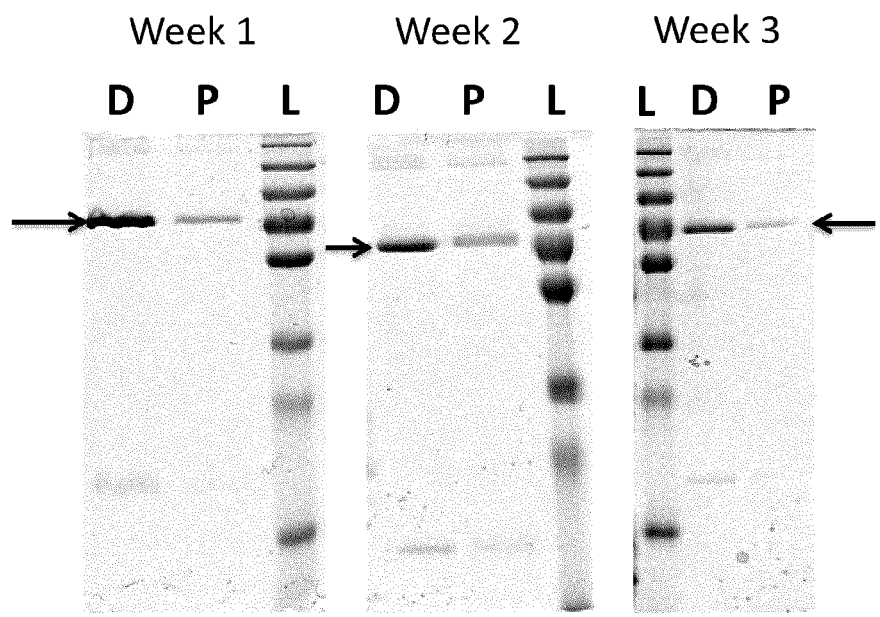

The inventors first confirmed that β-sheet peptides could stabilize purified AqpZ using a β-sheet peptide corresponding to BP1 disclosed by Tao et al. (i.e. structure (2)) The structure of AqpZ is comprised of six transmembrane helices and two half-membrane-spanning helices). Corresponding to this helical bundle structure, the circular dichroism (CD) spectrum of DDM-dissolved AqpZ displays signature α-helix absorbance bands, i.e., strong positive band at 198 nm and negative bands at both 210 nm and 224 nm (FIG. 7A)[9], which are signatures of an α-helix structure. Similarly, BP1:AqpZ also displays signature α-helix absorbance bands on its CD spectra with blue-shift peaks. Without being bound by theory, it is believed that the blue-shifting of the absorbance peaks is attributable to the binding of BP1 which affects the local optical environment. Moreover both BP1: AqpZ and AqpZ/DDM stored at 4° C. retained its secondary structure for four weeks (FIG. 7A) and oligomeric status (FIG. 7B, showing results of pseudo-native 12% SDS-PAGE) for at least 3 weeks.

Figure 8C:
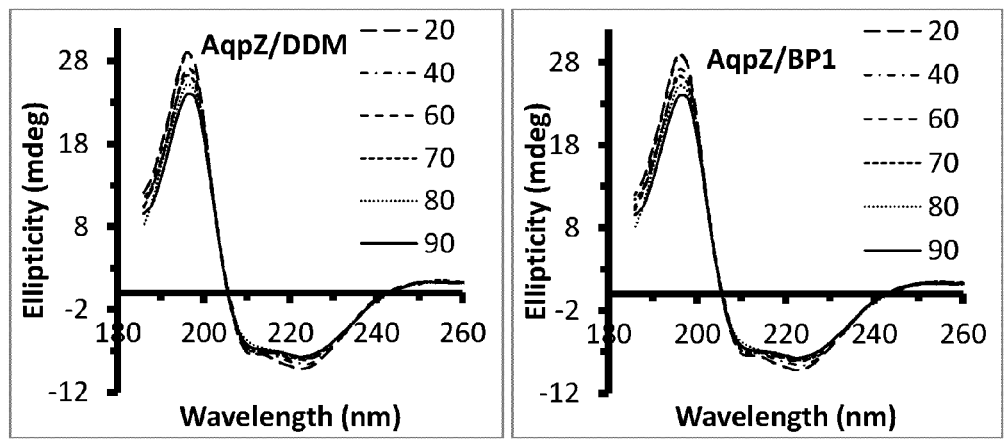
Figure 8C:
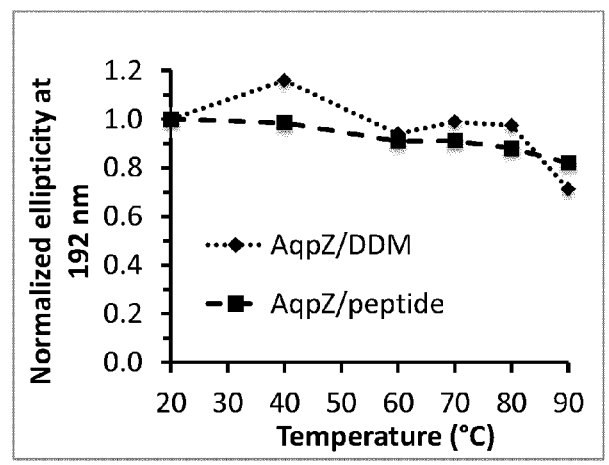
Figure 9A:
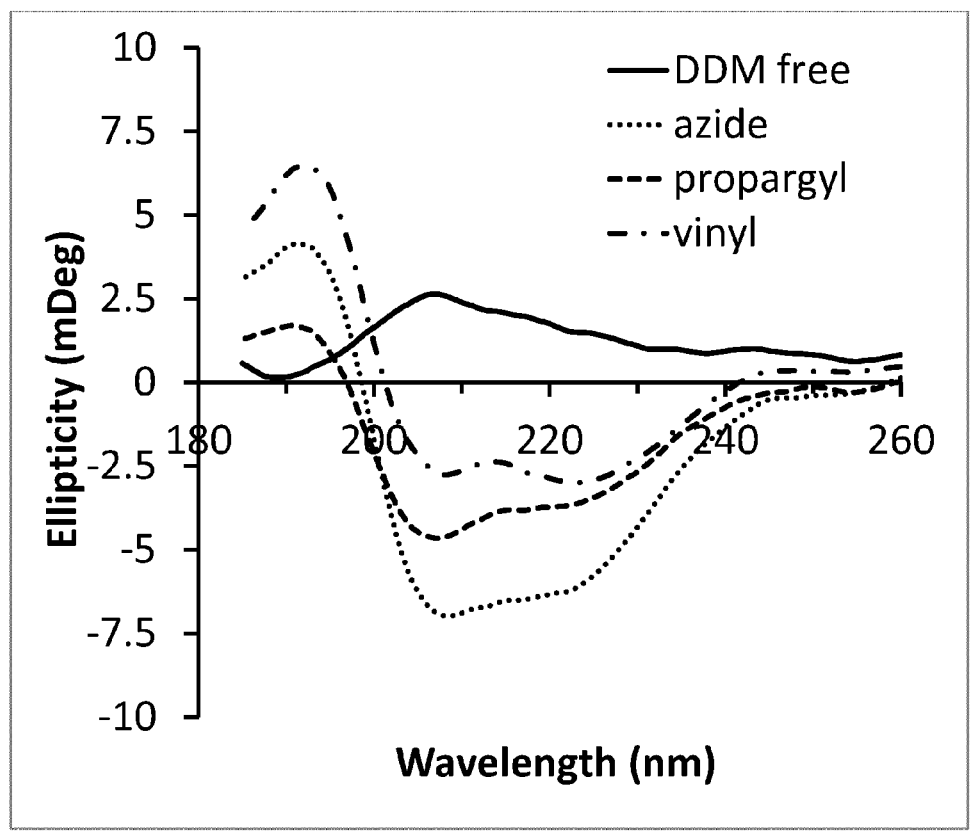
FIGS. 9A-9E show the stabilization of various proteins by three different functional β-sheet peptides. The proteins are AqpZ (FIG. 9A), $F_0F_1$-ATPase (FIG. 9B), NaChBac (FIG. 9C), ChIEF-mCitrine (FIG. 9D), and OmpG (FIG. 9E).
Figure 9B:
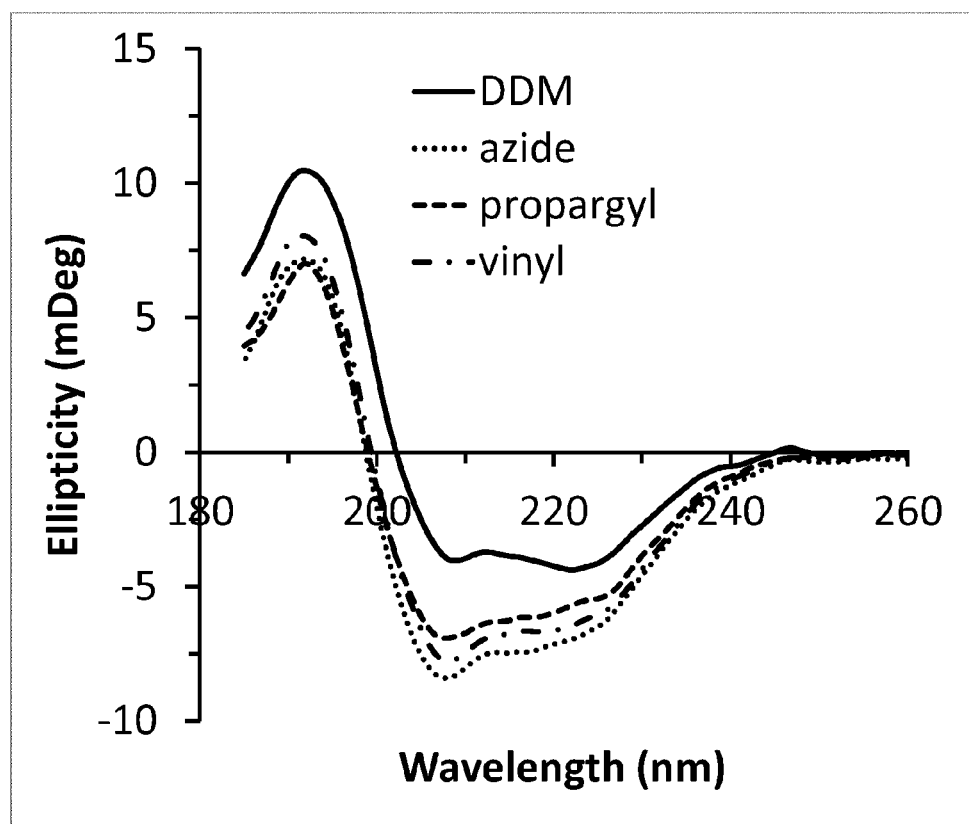
Figure 9C:
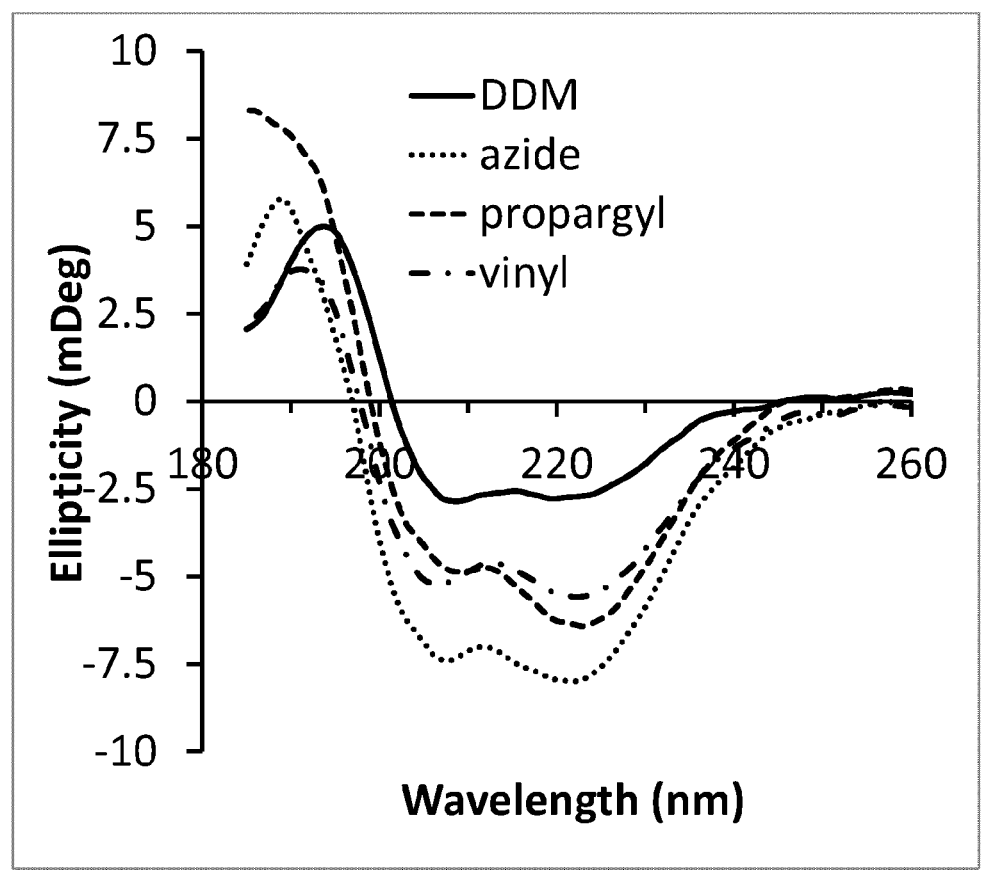
Figure 9D:
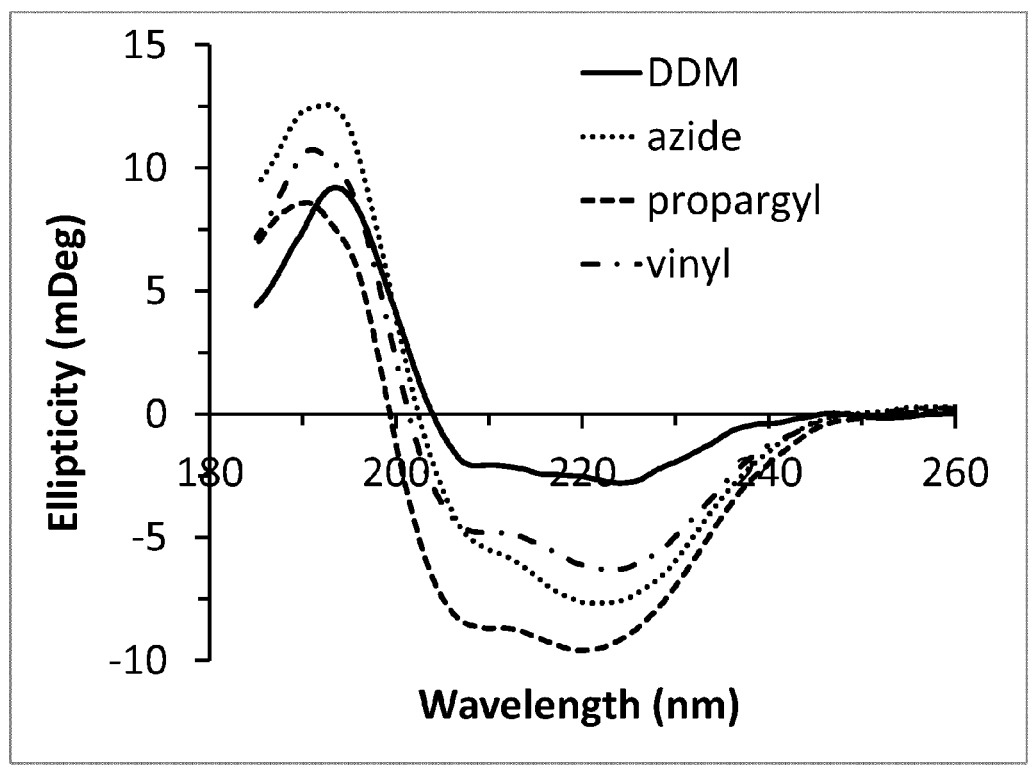
Figure 9E:
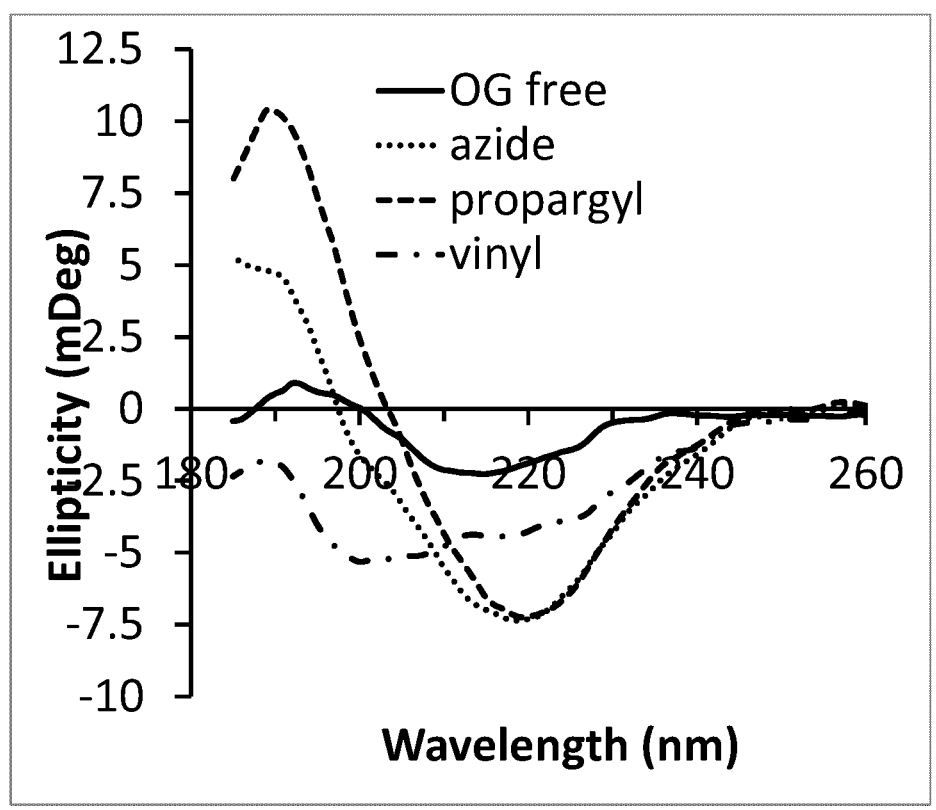

The inventors have further studied the thermostability of AqpZ/DDM and BP:AqpZ through monitoring their secondary structure on a CD spectrometer at different temperatures. As shown in FIGS. 8A-8C, like the DDM dissolved AqpZ (FIG. 8A), BP:AqpZ retains the majority (~70%) of its secondary structure at temperatures as high as 90° C. (FIG. 8B; normalized ellipticity for both DDM-stabilized and β-sheet peptide-stabilized AqpZ at 192 nm shown in FIG. 8C). This extraordinary thermostability suggests that BP1: AqpZ or the FBP1:AqpZ will be a good candidate for use in the manufacturing of a biomimetic water purification membrane, which might be exposed to harsh conditions of temperature or environmental contaminants such as salts, detergents, heavy metals, or the like.

Example 3.0—Stabilization of Membrane Proteins Using Functionalized β-Sheet Peptides The inventors have demonstrated that membrane proteins can be stabilized using functionalized β-sheet peptides. The additional membrane proteins tested include three membrane proteins having helix-bundle integral membrane proteins (ChIEF-mCitrine, NaChBac, and $F_0F_1$-ATPase) and one membrane protein having a beta-sheet integral membrane protein (OmpG). AqpZ is a helix-bundle integral membrane protein.

ChIEF is a laboratory-designed light-gated cation channel that transports protons, sodium ions, calcium ions, and the like upon stimulation with light. In this specific example, a fluorescent tag mCitrine was genetically attached to the C-terminus of the protein to facilitate purification, resulting in the ChIEF-mCitrine construct. NaChBac is a bacterial (*Bacillus halodurans*) membrane protein that transports sodium ions as regulated by membrane potential. $F_0F_1$-ATPase is an ATP synthase (from *Bacillus* PS3) that synthesizes ATP when driven by the proton gradient across the cell membrane. OmpG is a bacterial porin (*Escherichia coli* K12) that is capable of transporting large solutes such as disaccharides across the membranes.

Results for the stabilization of each protein are shown in FIGS. 9A-9E, respectively. Each of the above proteins was stabilized by three different functionalized β-sheet peptides (azide, propargyl and vinyl) having the sequence of BP1, corresponding to structures (6), (7) and (8), respectively. The CD spectra of each protein is shown, with either unstabilized protein (DDM free or OG free for AqpQ and OmpG, respectively), or with protein stabilized with DDM ($F_0F_1$-ATPase, NaChBac and ChIEF-mCitrine).

The inventors further demonstrated that $F_0F_1$-ATPase maintains its functionality when stabilized by functionalized β-sheet peptides by measuring its ATP-hydrolysis activity. The production of inorganic phosphate (Pi) in the enzymatic reaction serves an indicator of enzyme activity. The ATPase hydrolysis activity was performed using a PiColorLock™ phosphate detection reagent Kit (Innova Biosciences) following the manufacturer's instruction.

Figure 10A:
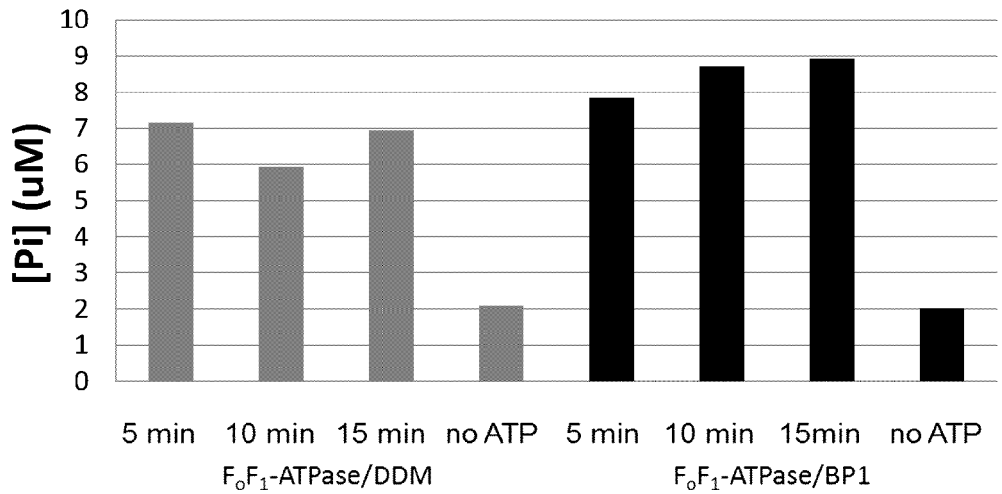
FIG. 10A shows that $F_0F_1$-ATPase maintains its functionality when stabilized by a β-sheet peptide.
Figure 10B:
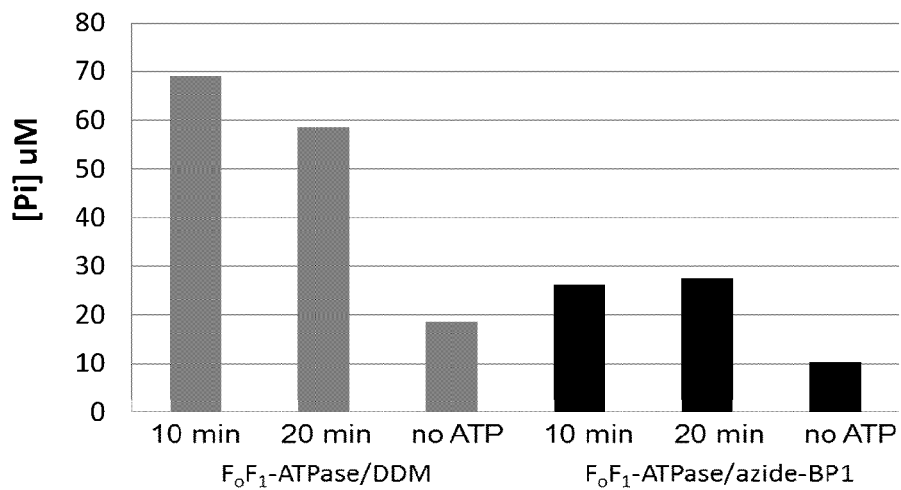
FIG. 10B shows that $F_0F_1$-ATPase maintains its functionality when stabilized by a functionalized β-sheet peptide.

As shown in FIG. 10A, the enzyme activity of $F_0F_1$-ATPase (characterized by its hydrolysis activity) is similar when stabilized with BP1 or by DDM. As shown in FIG. 10B, $F_0F_1$-ATPase also retains hydrolysis activity when stabilized by a functionalized β-sheet peptide, azide-BP1 having the structure (6). Thus, it can be soundly predicted that $F_0F_1$-ATPase stabilized by functionalized β-sheet peptides and incorporated into a membrane by reaction of the functional group of the functionalized β-sheet peptide with the membrane can be used to create an artificial ATP generation system. When a proton gradient presents across the membrane housing the $F_0F_1$-ATPase, the enzyme will synthesize ATP from ADP and inorganic phosphate, resulting in the generation of ATP on one side of the membrane. The enzyme can also be made to function in reverse to create a proton gradient from the hydrolysis of ATP. Thus, $F_0F_1$-ATPase could be used to synthesize ATP, or alternatively to pump protons from one side of a membrane having the $F_0F_1$-ATPase incorporated therein to the other side of the membrane.

AqpZ, NaChBac, ChIEF and ATPase are all proteins sharing a similar transmembrane domain structure that is formed by a helix bundle. OmpG represents an example of a different transmembrane domain structure: a beta-sheet barrel. Based on the fact that such a diverse set of membrane proteins, including AqpZ, were successfully stabilized with functionalized β-sheet peptides, and based on the high degree of conservation among different aquaporins, for example as shown in FIG. 1B, it can be soundly predicted that other aquaporins besides AqpZ can be stabilized with functionalized β-sheet peptides and coupled to membranes to remove contaminants from water. It can further be soundly predicted that functionalized β-sheet peptides can be used to stabilize and tether a variety of membrane proteins to make useful protein constructs. Based on the results showing that $F_0F_1$-ATPase retains its activity when stabilized by functionalized β-sheet peptides and showing that aquaporin can be incorporated into a membrane using functionalized β-sheet peptides and used to increase the flux of water through the membrane while limiting the passage of salt through the membrane as discussed in Example 4.0 below, it can be soundly predicted that other membrane proteins will maintain their functionality when stabilized by functionalized β-sheet peptides.

Example 4.0—Evaluation of Transport of Water Through Aquaporin-Containing Membranes Example 4.1—Synthesis of Polysulfone Membrane An azide-functionalized polysulfone membrane is prepared following the general reaction set forth in Scheme 2, as described in the literature (Yilmaz et al., 2011). In step 1, chloromethylation of polysulfone is initially done by dissolving in chloroform in a round-bottom flask equipped with a magnetic stirrer, reflux condenser and thermometer. The solution was heated at 50° C. under nitrogen atmosphere, and then p-formaldehyde (10 g), chlorotrimethylsilane (42.50 mL) and tin(IV)chloride (1.75 g) were added to the polymer solution. Once the reaction was completed (50 hours at 50° C.) the mixture was poured into methanol under stirring and the polymer precipitate was filtered, then washed well with methanol and finally dried in a vacuum oven at 60-65° C. for 24 hours.

In step 2, the chlorinated polysulfone is then dissolved in DMF with $NaN_3$ in a round-bottom flask placed in a heated bath and the reaction mixture stirred at 65° C. for 10 hours. The reaction mixture was cooled to room temperature and poured into methanol under stirring and the separated polymer was filtered, and washed with methanol. Polyvinylpyrrolidone (PVP) was added as a pore-forming agent prior to drying in a vacuum oven at 60° C. for 24 hours.

Example 4.2—Separation Properties of Synthesized Biomimetic Membranes

A membrane incorporating β-sheet peptide stabilized AqpZ was prepared using the polysulfone membrane prepared according to Example 4.1 and a β-sheet peptide having the structure (2). To functionalize the β-sheet peptide to form a polyamide-polysulfone composite membrane structure, M-phenylene-diamine concentration (MPD) (2 wt %) was combined with trimesoyl chloride (TMC) (0.15 wt %) together with AqpZ and the polysulfone membrane to yield an interlocking interfacial polymerized polyamide layer on the polysulfone membrane. The reaction time (interfacial polymerization of functionalized β-sheet peptide stabilized protein on the membrane) was 15 seconds, and the AqpZ concentration (present in the protein solution used to carry out the interfacial polymerization) was 0.033 mg/mL, with 0.064 mg/mL of β-sheet peptide. Conditions were the same for the membrane tested without AqpZ, except that AqpZ was not present.

Separation properties of the synthesized biomimetic membranes were characterized in a standard cross flow reverse osmosis setup. Briefly, a membrane coupon with an active surface area of 42 cm² was mounted in the test cell (CF42 Membrane Cell, Sterlitech). The feed solution (1 g/L NaCl at 25° C.) (1000 ppm) was pumped at a constant cross flow of 0.8 gallons per minute. Membranes were compacted for 2 hours at the desired testing pressure before sample collection for water flux and rejection measurements. Membrane permeate flux (Jv) was determined using the gravimetric method, and NaCl rejection (R) was obtained based on conductivity measurements of the permeate and feed water.

Figure 11A:
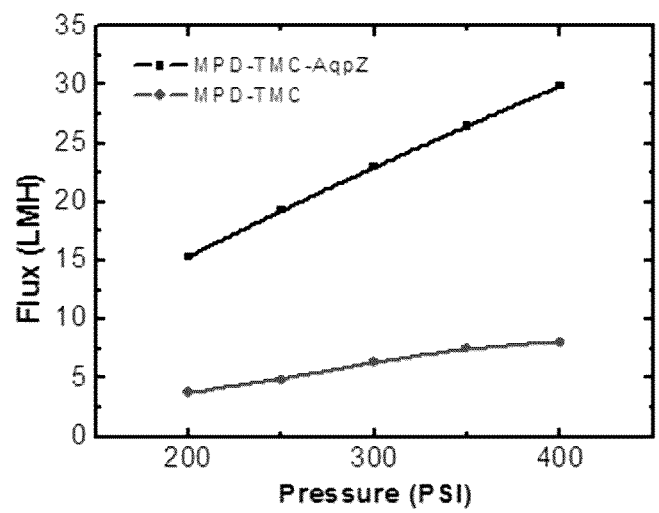
FIG. 11A shows the flux of water through a membrane being used to remove sodium chloride from water, with and without AqpZ.
Figure 11B:
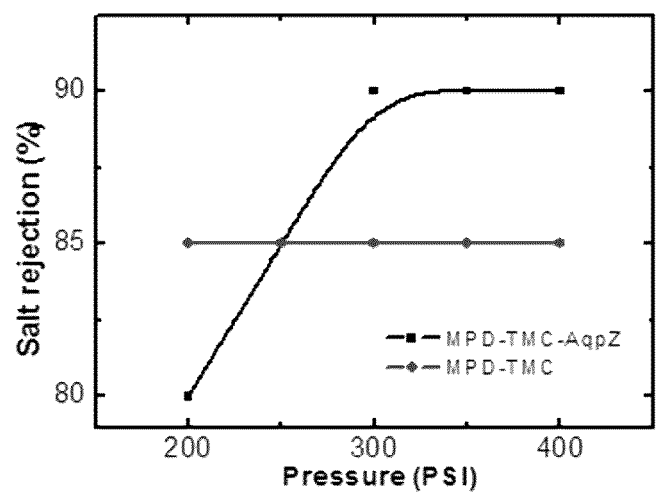
FIG. 11B shows salt rejection by a membrane being used to remove sodium chloride from water, with and without AqpZ.
Figure 11C:
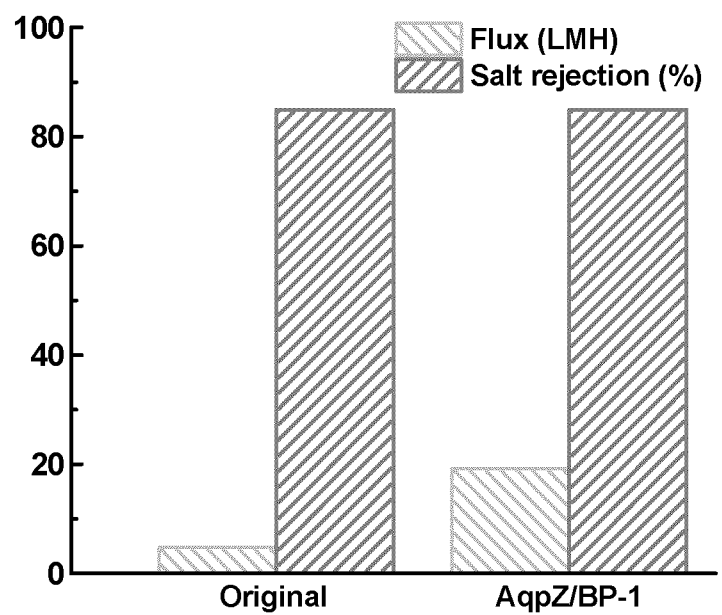
FIG. 11C depicts graphically the flux and salt rejection achieved by a membrane construct incorporating no protein ("Original") as compared with a membrane incorporating AqpZ, at an operating pressure of 250 PSI.

As summarized in Table 3 (with AqpZ) and Table 4 (without AqpZ) and shown in FIGS. 11A, 11B and 11C (FIG. 11C shows data only at the 250 PSI operating pressure), flux (liters per square meter per hour, or LMH) (i.e. the rate of flow of water through the membrane) was increased in the construct incorporating aquaporin, and, at higher operating pressures, greater salt rejection was achieved when aquaporin was present. These results demonstrate that a membrane incorporating aquaporin can be used to enhance the separation of water from an undesired solution component such as sodium chloride by increasing the flux (i.e. rate of flow of water through the membrane) while maintaining the rejection of sodium chloride by the membrane (i.e. while continuing to impede the passage of sodium chloride through the membrane).

TABLE 3

Flux and salt rejection by a membrane construct incorporating AqpZ.

| pressure (PSI) | flux (LMH) | salt rejection (%) |
|---|---|---|
| 200 | 15.35 | 80 |
| 250 | 19.33 | 85 |
| 300 | 22.99 | 90 |
| 350 | 26.52 | 90 |
| 400 | 29.92 | 90 |

TABLE 4

Flux and salt rejection by a control membrane construct without AqpZ.

| pressure (PSI) | flux (LMH) | salt rejection (%) |
|---|---|---|
| 200 | 3.74 | 85 |
| 250 | 4.86 | 85 |
| 300 | 6.33 | 85 |
| 350 | 7.52 | 85 |
| 400 | 8.05 | 85 |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

REFERENCES

The following references may be of interest with respect to the subject matter described herein. Each of the following references is expressly incorporated herein by reference in its entirety for all purposes.
1. S. Gnidehou et al., Expression in *Escherichia coli* and purification of human recombinant connexin-43, a four-pass transmembrane protein. *Protein expression and purification* 78, 174 (August, 2011).
2. C. Tribet, R. Audebert, J. L. Popot, Amphipols: polymers that keep membrane proteins soluble in aqueous solutions. *Proc Natl Acad Sci USA* 93, 15047 (Dec. 24, 1996).
3. T. H. Bayburt, Y. V. Grinkova, S. G. Sligar, Self-Assembly of Discoidal Phospholipid Bilayer Nanoparticles with Membrane Scaffold Proteins. *Nano Letters* 2, 4 (2002).
4. X. Zhao et al., Designer short peptide surfactants stabilize G protein-coupled receptor bovine rhodopsin. *Proc Natl Acad Sci USA* 103, 17707 (Nov. 21, 2006).
5. P. S. Chae et al., Maltose-neopentyl glycol (MNG) amphiphiles for solubilization, stabilization and crystallization of membrane proteins. *Nature methods* 7, 1003 (December, 2010).
6. H. Tao et al., Engineered nanostructured beta-sheet peptides protect membrane proteins. *Nature methods* 10, 759 (August, 2013).
M. J. Borgnia, D. Kozono, G. Calamita, P. C. Maloney, P. Agre, Functional reconstitution and characterization of AqpZ, the *E. coli* water channel protein. *Journal of molecular biology* 291, 1169 (Sep. 3, 1999).
8. D. F. Savage, P. F. Egea, Y. Robles-Colmenares, J. D. O'Connell, 3rd, R. M. Stroud, Architecture and selectivity in aquaporins: 2.5 a X-ray structure of aquaporin Z. *PLoS biology* 1, E72 (December, 2003).
9. S. M. Kelly, T. J. Jess, N. C. Price, How to study proteins by circular dichroism. *Biochimica et biophysica acta* 1751, 119 (Aug. 10, 2005).
10. Erbakan, M., Shen, Y.-X., Grzelakowski, M., Butler, P. J., Kumar, M., & Curtis, W. R. (2014). Molecular cloning, overexpression and characterization of a novel water channel protein from *Rhodobacter sphaeroides*. *PloS One*, 9(1), e86830.
11. Sun, G., Zhou, H., Li, Y., Jeyaseelan, K., Armugam, A., & Chung, T.-S. (2012). A novel method of AquaporinZ incorporation via binary-lipid Langmuir monolayers. *Colloids and Surfaces B: Biointerfaces*, 89, 283-288.

12. Sun, G., Chung, T.-S., Jeyaseelan, K., & Armugam, A. (2013). A layer-by-layer self-assembly approach to developing an aquaporin-embedded mixed matrix membrane. *RSC Adv.*, 3(2), 473-481.
13. Evram, E., et al. (1997). Polymers with pendant functional group. III. Polysulfones containing viologen group. *J. Macromol. Sci., A Pure Appl Chem* 34:1701-1714.
14. Habibi, Y. (2014). Key advances in the chemical modification of nanocelluloses. *Chemical Society Reviews*, 43(5), 1519-1542.
15. Habel, J., Hansen, M., Kynde, S., Larsen, N., Midtgaard, S., Jensen, G., et al. (2015). Aquaporin-Based Biomimetic Polymeric Membranes: Approaches and Challenges. *Membranes*, 5(3), 307-351.
16. Yilmaz, G. et al. (2011). Modification of polysulfones by click chemistry: Amphiphilic graft copolymers and their protein adsorption and cell adhesion properties. *J. Pol. Sci.: Part A: Pol. Chem.*, 49, 110-117.
17. Ghosh et al., "Impacts of support membrane structure and chemistry on polyamide-polysulfone interfacial composite membranes", 2009, *J. Mem. Sci*, 336, 140-148.

Sequence Listing Free Text

This specification includes an electronic sequence listing, which is expressly incorporated as part of this specification. This sequence listing includes free text as follows:

SEQ ID NO:1—BP1—Synthetic peptide
SEQ ID NO:12—C-Propargyl-BP1—Synthetic peptide
SEQ ID NO:13—N-azido-BP1—Synthetic peptide
SEQ ID NO:14—N-Propargyl-BP1—Synthetic peptide
SEQ ID NO:15—Vinyl-BP1—Synthetic peptide
SEQ ID NO:16—pET28a-ApqZ—Plasmid used for expression of AqpZ in *Eschericia coli*

What is claimed is:

1. A membrane configured for selectively passing desired particles across the membrane comprising:
a support; and
a plurality of membrane protein molecules associated with the support, each one of the membrane protein molecules being stabilized by a plurality of functionalized β-sheet peptides, each one of the functionalized β-sheet peptides comprising at least one functional group, the functionalized β-sheet peptides being linked to the support via at least one of the at least one functional groups,
wherein the functionalized β-sheet peptides comprise at least eight alternating polar and apolar amino acid residues with a hydrophobic moiety at each end and do not comprise a hydrophobin; and
wherein the at least one functional group comprises an azide, an alkyne, an alkene, a vinyl, an azidophenyl, a thiol, a cyclopropyl, or an amido group, or wherein the at least one functional group is provided by a bifunctional crosslinker.

2. The membrane as defined in claim 1, wherein at least some of the functionalized β-sheet peptides are covalently linked to the support.

3. The membrane as defined in claim 1, wherein the membrane protein molecules are selected from group consisting of aquaporin, ChIEF, $F_0F_1$-ATPase, OmpG, NaChBAc, bacteriorhodopsin, alamethicin, hemolysin, NADH reductase, OmpF, RC (photosynthetic reaction centre), NtAPQ1, NtPIP2:1, AQP0, AQP10, SoPIP2, TsX, gramicidin A, MloK1, LamB, FhuA, ATPase, hemagglutinin, cytochrome C oxidase, polymyxin B, cecropinA and proteorhodopsin.

4. The membrane as defined claim 1, wherein the membrane protein molecules form a plurality of channels in the membrane to selectively permit passage of the desired particles therethrough.

5. The membrane as defined in claim 1, wherein the membrane protein molecules are stabilized by the functionalized β-sheet peptides to allow the membrane protein molecules to selectively transport the desired particles across the membrane.

6. The membrane as defined in claim 1, wherein the support is a matrix for immobilizing the complex comprising the membrane protein molecules stabilized by the functionalized β-sheet peptides.

7. The membrane as defined in claim 1, wherein the membrane protein molecules comprise aquaporin and the desired particles comprise water molecules.

8. The membrane as defined in claim 1, wherein:
the membrane protein molecules comprise ChIEF and the desired particles comprise protons, sodium ions, or calcium ions; or
the membrane protein molecules comprise $F_0F_1$-ATPase and the desired particles comprise ATP or protons; or
the membrane protein molecules comprise OmpG and the desired particles comprise disaccharides; or
the membrane protein molecules comprise NaChBAc and the desired particles comprise sodium ions; or
the membrane protein molecules comprise alpha-hemolysin, MspA (*Mycobacterium smegmatis* porin A), OmpF or OmpG and the desired particles comprise polynucleotides; or
the membrane protein molecules comprise alamethicin, hemolysin, NADH reductase, OmpG, OmpF or photosynthetic reaction centre and the desired particles comprise electrons; or
the membrane protein molecules comprise alamethicin and the desired particles comprise calcium or calcein; or
the membrane protein comprises NtAPQ1 or NtPIP2:1 and the desired particles comprise carbon dioxide; or
the membrane protein comprises AQP0, AQP10 or SoPIP2; 1 and the desired particles comprise water; or
the membrane protein comprises TsX and the desired particles comprise nucleosides; or
the membrane protein comprises OmpF and the desired particles comprise acridine orange, paraquat, pyocyanin, actylthiocholine, enone, ELF97, 7-ADCA, PGME, nucleosides, ampicillin, L-ascorbic acid, CO, $Na_2S_2O_4$, or $ONOO^-$; or
the membrane protein comprises gramicidin A and the desired particles comprise monovalent cations; or
the membrane protein comprises LamB and the desired particles comprise sugars or DNA; or
the membrane protein comprises FhuA and the desired particles comprise sulphorhodamine B, 3,3',5,5'-tetramethylbenzidine, NAD, DNA, or calcein; or
the membrane protein comprises bacteriorhodopsin, proteorhodopsin, or both bacteriorhodopsin and cytochrome C oxidase and the desired particles comprise $H^+$; or
the membrane protein comprises both bacteriorhodopsin and ATPase and the desired particles comprise $H^+$ and electrons; or
the membrane protein comprises cytochrome C oxidase and the desired particles comprise electrons; or
the membrane protein comprises cecropinA, polymyxin B, or hemolysin and the desired particles comprise calcein.

9. The membrane as defined in claim 1, wherein the support comprises a polymer, carbon nanotube mesh, or nanocrystalline cellulose, and wherein the polymer comprises polysulfone, polycarbonate, or polylactone.

10. The membrane as defined in claim 1, wherein the membrane protein comprises aquaporin, and wherein the membrane is configured to impede passage of sodium ions, chloride ions, ammonia, urea, dye, pesticides, pharmaceutical waste, and other organic compounds while selectively permitting passage of water through the membrane.

11. A complex comprising a membrane protein stabilized by a plurality of functionalized β-sheet peptides, each one of the functionalized β-sheet peptides comprising at least one functional group, wherein the β-sheet peptides comprise at least eight alternating polar and apolar amino acid residues with a hydrophobic moiety at each end and do not comprise a hydrophobin; and wherein the at least one functional group comprises an azide, an alkyne, an alkene, a vinyl, an azidophenyl, a thiol, a cyclopropyl, or an amido group, or wherein the at least one functional group is provided by a bifunctional crosslinker.

12. The complex as defined in claim 11, wherein the complex is immobilized on a solid support by conjugation of at least one of the at least one functional groups on at least one of the plurality of functionalized β-sheet peptides to the solid support.

13. The membrane as defined in claim 1, wherein the functionalized β-sheet peptides comprise the amino acid sequence of SEQ ID NO:1, wherein optionally one or more amino acids comprises an N-methyl amino acid.

14. The membrane as defined in claim 1, wherein the functional group on the functionalized β-sheet peptides comprises an azide, an alkyne, an alkene, a vinyl, an azidophenyl, or a thiol.

15. The membrane as defined in claim 1, wherein the functionalized β-sheet peptides comprise the structure (I), (II), (III), (IV), (V) or (VI):

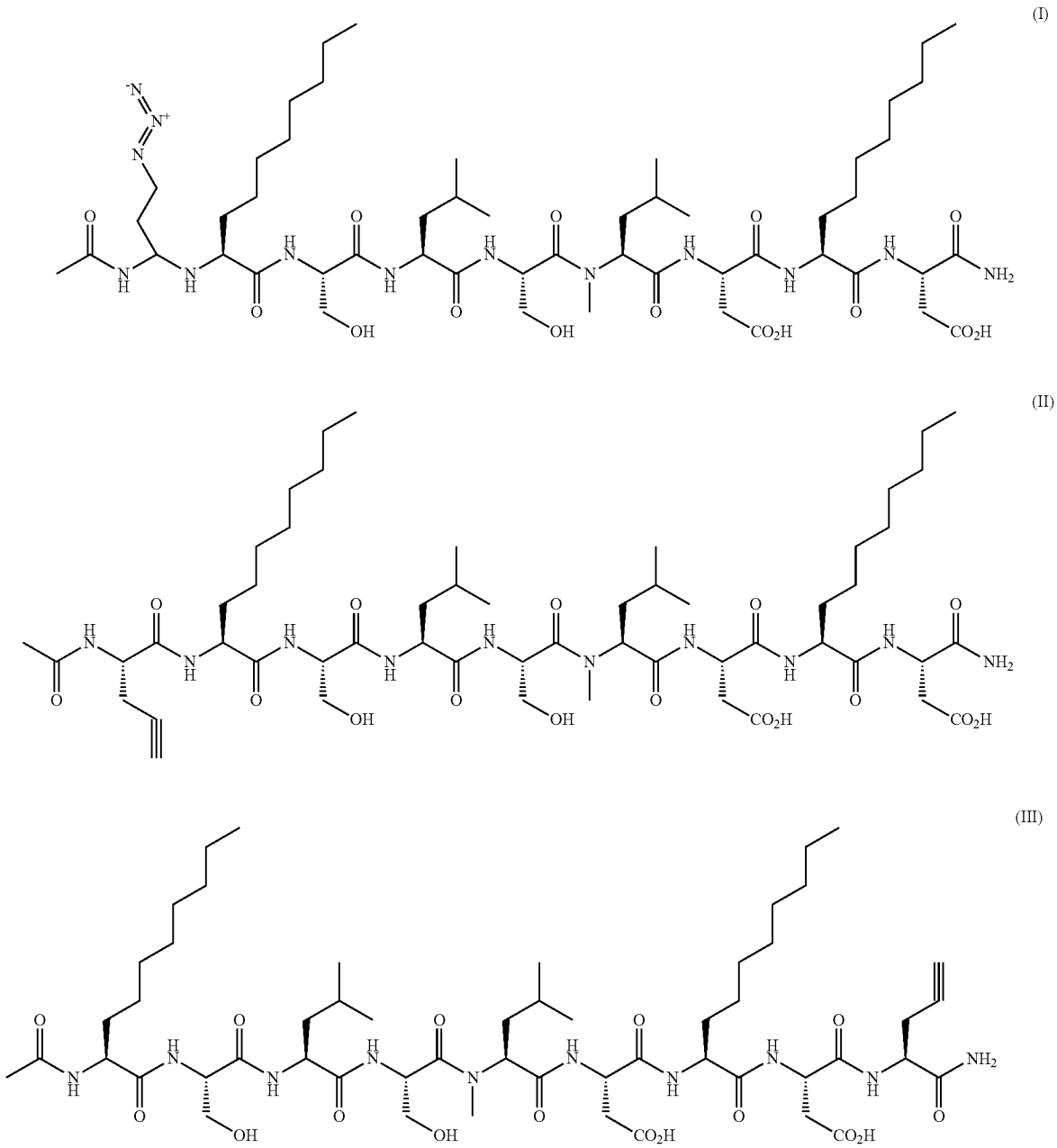

(IV)

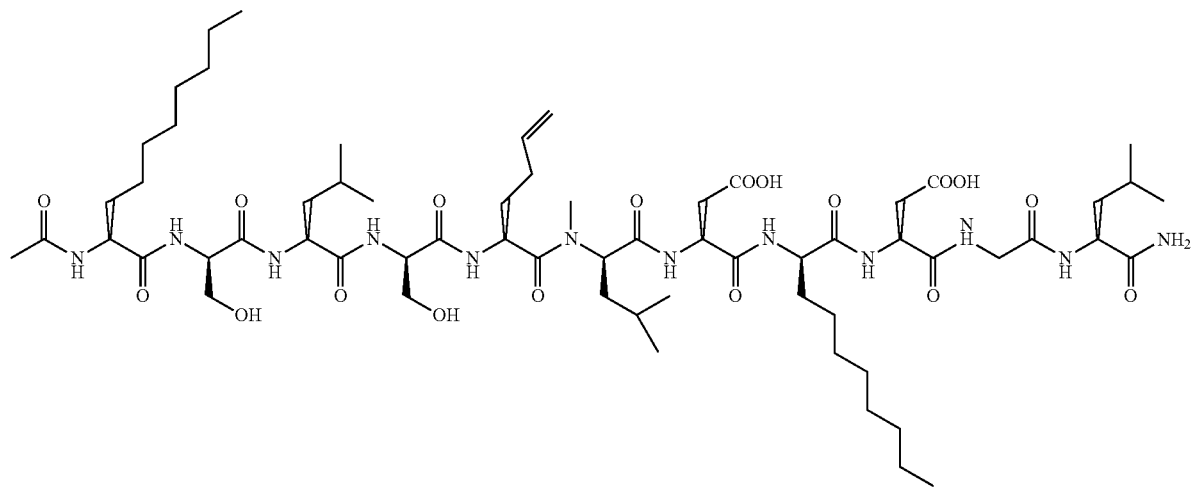

(V)

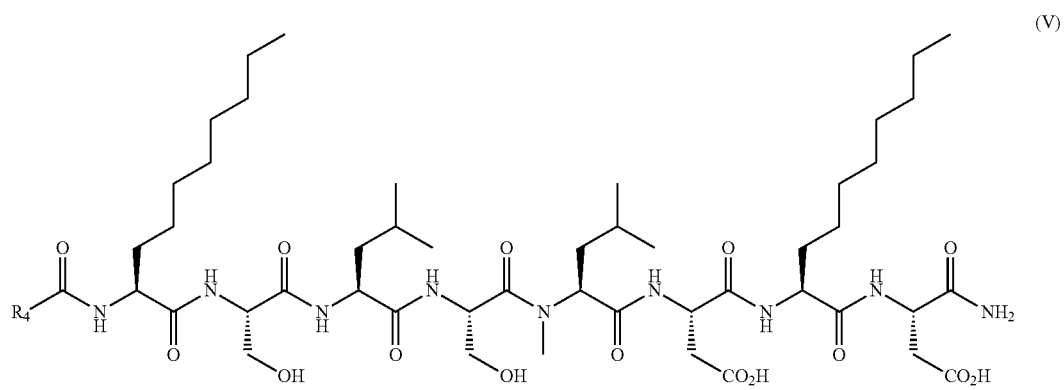

(VI)

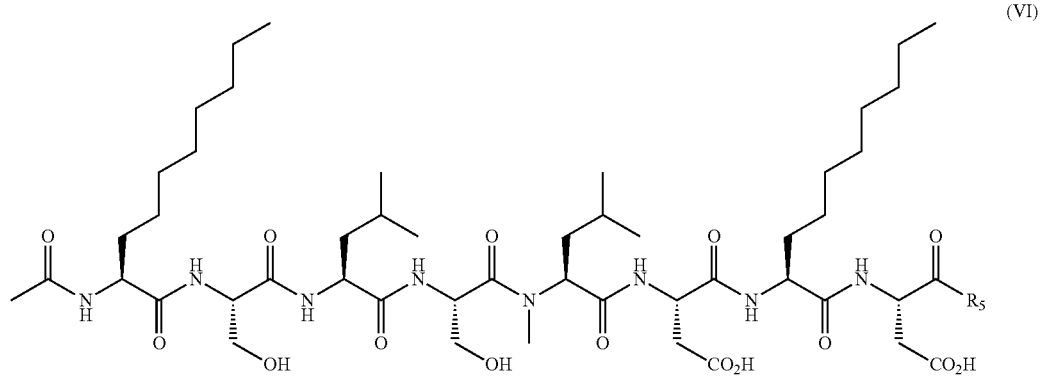

wherein $R_4$ and $R_5$ are independently an azide group, alkyne group, alkene group, thio group, azidophenyl group, or vinyl group.

16. The membrane as defined in claim 1, wherein the at least one functional group of the functionalized β-sheet peptides is provided by the bifunctional crosslinker, and wherein the bifunctional crosslinker comprises a photoreactive functional group.

17. The membrane as defined in claim 1, wherein the plurality of membrane protein molecules comprise aquaporin, and the aquaporin comprises AqpZ.

18. The membrane as defined in claim 1, wherein the functionalized β-sheet peptides comprise an amino acid sequence as set forth in any one of SEQ ID NO:1, SEQ ID NO:12, SEQ ID NO:13, SEQ ID NO:14, or SEQ ID NO:15.

19. The membrane as defined in claim 1, wherein the functionalized β-sheet peptides comprise an amino acid sequence having from N-terminal to C-terminal:
- at position 1, octyl(Gly) or octyl(Ala);
- at position 2, Ser, Thr or Cys;
- at position 3, Leu, Ile or Val;
- at position 4, Ser, Thr or Cys;
- at position 5, Leu, Ile or Val;
- at position 6, Asp, Asn, Glu, Gln or His;
- at position 7, octyl(Gly) or octyl(Ala); and
- at position 8, Asp, Asn, Glu, Gln or His.

20. The membrane as defined in claim 4, wherein the channel is formed in a pore in the membrane.

* * * * *

```
SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (octyl)Gly
<220> FEATURE:
<221> NAME/KEY: MOD_RES
<222> LOCATION: (7)..(7)
<223> OTHER INFORMATION: (octyl)Gly

<400> SEQUENCE: 1

Xaa Ser Leu Ser Leu Asp Xaa Asp
1               5

<210> SEQ ID NO 2
<211> LENGTH: 243
<212> TYPE: PRT
<213> ORGANISM: Rhodobacter sphaeroides

<400> SEQUENCE: 2

Met Thr Lys Lys Leu Leu Ala Glu Leu Leu Gly Thr Phe Ile Leu Val
1               5                   10                  15

Phe Phe Gly Cys Gly Ala Ala Val Leu Met Gly Pro Gln Ile Gly Met
                20                  25                  30

Leu Gly Ile Ser Leu Ala Phe Gly Leu Ser Ile Val Ala Ala Ala Tyr
            35                  40                  45

Ser Leu Gly Ala Ile Ser Gly Ala His Leu Asn Pro Ala Val Ser Leu
        50                  55                  60

Gly Phe Leu Met Ala Gly Arg Met Pro Met Ala Glu Phe Gly Gly Tyr
65                  70                  75                  80

Val Leu Ala Gln Ile Ala Gly Ala Leu Leu Gly Ser Leu Val Val Phe
                85                  90                  95

Leu Ile Ala Ser Gly Lys Ala Gly Tyr Val Leu Ala Thr Asp Gly Leu
            100                 105                 110

Gly Gln Asn Gly Phe Gly Ala Gly Tyr Leu Gly Glu Tyr Ser Met Gly
        115                 120                 125

Ala Ala Leu Ile Phe Glu Leu Ile Ala Thr Phe Val Phe Val Ser Val
        130                 135                 140
```

Ile Leu Ala Ala Thr Ala Ser His Val Ser Ala Ser Thr Ala Leu
145                 150                 155                 160

Ala Gly Leu Ala Ile Gly Leu Thr Leu Thr Gly Ile His Leu Val Gly
                165                 170                 175

Ile Asn Val Thr Gly Val Ser Val Asn Pro Ala Arg Ser Leu Ala Pro
            180                 185                 190

Ala Leu Phe Val Gly Gly Lys Ala Leu Ser Asp Leu Trp Val Phe Ile
        195                 200                 205

Val Ala Pro Leu Ala Gly Gly Ala Ala Gly Leu Ala His Ala Ser
    210                 215                 220

Gly Phe Phe Arg Pro Gly Gly Ile Glu Pro Ala Pro Ala Thr Gly Ala
225                 230                 235                 240

Ala Thr Leu

<210> SEQ ID NO 3
<211> LENGTH: 231
<212> TYPE: PRT
<213> ORGANISM: Escherichia coli

<400> SEQUENCE: 3

Met Phe Arg Lys Leu Ala Ala Glu Cys Phe Gly Thr Phe Cys Leu Val
1               5                   10                  15

Phe Gly Gly Cys Gly Ser Ala Val Leu Pro Ala Gly Phe Pro Glu Leu
            20                  25                  30

Gly Ile Gly Phe Ala Gly Val Ala Leu Ala Phe Gly Leu Thr Val Leu
        35                  40                  45

Thr Met Ala Phe Ala Val Gly His Ile Ser Gly Gly His Phe Asn Pro
50                  55                  60

Ala Val Thr Ile Gly Leu Trp Ala Gly Gly Arg Phe Pro Ala Lys Glu
65                  70                  75                  80

Val Val Gly Tyr Val Ile Ala Gln Val Val Gly Gly Ile Val Ala Ala
                85                  90                  95

Ala Leu Leu Tyr Leu Ile Ala Ser Gly Lys Thr Gly Phe Asp Ala Ala
            100                 105                 110

Ala Ser Gly Phe Ala Ser Asn Gly Tyr Gly Glu His Ser Pro Gly Gly
        115                 120                 125

Tyr Ser Met Leu Ser Ala Leu Val Val Glu Leu Val Leu Ser Ala Gly
130                 135                 140

Phe Leu Leu Val Ile His Gly Ala Thr Asp Lys Phe Ala Pro Ala Gly
145                 150                 155                 160

Phe Ala Pro Ile Ala Ile Gly Leu Ala Leu Thr Leu Ile His Leu Ile
                165                 170                 175

Ser Ile Pro Val Thr Asn Thr Ser Val Asn Pro Ala Arg Ser Thr Ala
            180                 185                 190

Val Ala Ile Phe Gln Gly Gly Trp Ala Leu Glu Gln Leu Trp Phe Phe
        195                 200                 205

Trp Val Val Pro Ile Val Gly Gly Ile Ile Gly Gly Leu Ile Tyr Arg
210                 215                 220

Thr Leu Leu Glu Lys Arg Asp
225                 230

<210> SEQ ID NO 4
<211> LENGTH: 281
<212> TYPE: PRT
<213> ORGANISM: Escherichia coli

<400> SEQUENCE: 4

```
Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
                100                 105                 110

Phe Asp Phe Glu Gln Thr His His Ile Val Arg Gly Ser Val Glu Ser
            115                 120                 125

Val Asp Leu Ala Gly Thr Phe Ser Thr Tyr Pro Asn Pro His Ile Asn
130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
                180                 185                 190

Ser Met Gly Pro Leu Thr Gly Phe Ala Met Asn Pro Ala Arg Asp Phe
            195                 200                 205

Gly Pro Lys Val Phe Ala Trp Leu Ala Gly Trp Gly Asn Val Ala Phe
        210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
                260                 265                 270

Thr Pro Ser Glu Gln Lys Ala Ser Leu
            275                 280
```

<210> SEQ ID NO 5
<211> LENGTH: 246
<212> TYPE: PRT
<213> ORGANISM: Methanobacter marburgensis

<400> SEQUENCE: 5

```
Met Val Ser Leu Thr Lys Arg Cys Ile Ala Glu Phe Ile Gly Thr Phe
1               5                   10                  15

Ile Leu Val Phe Phe Gly Ala Gly Ser Ala Ala Val Thr Leu Met Ile
            20                  25                  30

Ala Ser Gly Gly Thr Ser Pro Asn Pro Phe Asn Ile Gly Ile Gly Leu
        35                  40                  45

Leu Gly Gly Leu Gly Asp Trp Val Ala Ile Gly Leu Ala Phe Gly Phe
    50                  55                  60

Ala Ile Ala Ala Ser Ile Tyr Ala Leu Gly Asn Ile Ser Gly Cys His
65                  70                  75                  80
```

```
Ile Asn Pro Ala Val Thr Ile Gly Leu Trp Ser Val Lys Lys Phe Pro
                85                  90                  95

Gly Arg Glu Val Val Pro Tyr Ile Ile Ala Gln Leu Leu Gly Ala Ala
            100                 105                 110

Phe Gly Ser Phe Ile Phe Leu Gln Cys Ala Gly Ile Gly Ala Ala Thr
        115                 120                 125

Val Gly Gly Leu Gly Ala Thr Ala Pro Phe Pro Gly Ile Ser Tyr Trp
130                 135                 140

Gln Ala Met Leu Ala Glu Val Val Gly Thr Phe Leu Leu Met Ile Thr
145                 150                 155                 160

Ile Met Gly Ile Ala Val Asp Glu Arg Ala Pro Lys Gly Phe Ala Gly
                165                 170                 175

Ile Ile Ile Gly Leu Thr Val Ala Gly Ile Ile Thr Thr Leu Gly Asn
            180                 185                 190

Ile Ser Gly Ser Ser Leu Asn Pro Ala Arg Thr Phe Gly Pro Tyr Leu
        195                 200                 205

Asn Asp Met Ile Phe Ala Gly Thr Asn Leu Trp Asn Tyr Tyr Pro Ile
210                 215                 220

Tyr Val Ile Gly Pro Ile Val Gly Ala Val Leu Ala Ala Leu Thr Tyr
225                 230                 235                 240

Gln Tyr Leu Thr Ser Glu
                245

<210> SEQ ID NO 6
<211> LENGTH: 269
<212> TYPE: PRT
<213> ORGANISM: Synechococcus elongatus

<400> SEQUENCE: 6

Met Lys Met Leu Arg Ala Leu Lys His His Trp Pro Glu Tyr Leu Ile
1               5                   10                  15

Glu Ala Trp Gly Leu Gly Leu Phe Met Val Ala Ala Gly Val Val Gly
            20                  25                  30

Thr Leu Val Phe Tyr Pro Gln Ser Pro Ala Tyr Gln Ala Ile Ala Asp
        35                  40                  45

Pro Phe Leu Gln Arg Val Val Met Gly Leu Gly Met Gly Leu Thr Ala
    50                  55                  60

Met Ile Ile Met Tyr Ser Pro Trp Gly Lys Arg Ser Gly Ala His Ile
65                  70                  75                  80

Asn Pro Ala Val Thr Leu Thr Phe Tyr Arg Leu Lys Lys Ile Ala Ala
                85                  90                  95

Trp Asp Ala Phe Phe Tyr Val Val Phe Gln Phe Ile Gly Gly Leu Leu
            100                 105                 110

Gly Val Val Leu Val Ala Phe Leu Leu Gln Thr Pro Phe Thr Gln Ala
        115                 120                 125

Pro Val Asn Tyr Val Val Thr Val Pro Gly Lys Gln Gly Ala Ile Val
    130                 135                 140

Ala Cys Ile Ala Glu Tyr Phe Ile Ala Val Leu Met Met Ser Met Val
145                 150                 155                 160

Leu Phe Thr Ser Asn Gln Pro Lys Leu Glu Arg Phe Thr Pro Phe Phe
                165                 170                 175

Ala Gly Cys Leu Ile Val Ser Tyr Val Ile Phe Glu Ser Pro Leu Ser
            180                 185                 190

Gly Phe Gly Met Asn Pro Ala Arg Thr Val Ala Ser Ala Leu Pro Ser
```

```
                195                 200                 205
Gly Ile Trp Thr Ala Ile Trp Leu Tyr Phe Leu Ala Pro Ile Ala Gly
    210                 215                 220

Met Leu Thr Ala Ala Glu Leu Tyr Leu Arg Met Ile Gly Pro Arg Lys
225                 230                 235                 240

Ile Phe Cys Ala Lys Leu Tyr His Asp Pro Leu Tyr Arg Cys Ile His
                245                 250                 255

Cys Gly His Leu Ile His Trp His Arg Pro His Leu Arg
                260                 265

<210> SEQ ID NO 7
<211> LENGTH: 279
<212> TYPE: PRT
<213> ORGANISM: Pichia pastoris

<400> SEQUENCE: 7

Met Pro Asp Ile Glu Asn Gln Ala Ala Asp Gly Gln Ala Glu Ile Lys
1               5                   10                  15

Pro Glu Asp Ala Pro Tyr Ile Thr Asn Ala Tyr Lys Pro Ala Tyr Ala
                20                  25                  30

Arg Trp Gly Phe Gly Ser Asp Ser Val Arg Asn His Phe Ile Ala Met
            35                  40                  45

Ser Gly Glu Phe Val Gly Thr Phe Leu Phe Leu Trp Ser Ala Phe Val
        50                  55                  60

Ile Ala Gln Ile Ala Asn Gln Ala Pro Glu Thr Pro Asp Gly Gly Ser
65                  70                  75                  80

Asn Pro Ala Gln Leu Ile Met Ile Ser Phe Gly Phe Gly Phe Gly Val
                85                  90                  95

Met Val Gly Val Phe Ile Thr Tyr Arg Val Ser Gly Gly Asn Leu Asn
                100                 105                 110

Pro Ala Val Thr Leu Ala Leu Val Leu Ala Arg Ala Ile Pro Pro Phe
            115                 120                 125

Arg Gly Ile Leu Met Ala Phe Thr Gln Ile Val Ala Gly Met Ala Ala
        130                 135                 140

Ala Gly Ala Ala Ser Ala Met Thr Pro Gly Glu Ile Ala Phe Ala Asn
145                 150                 155                 160

Ala Leu Gly Gly Gly Ala Ser Arg Thr Arg Gly Leu Phe Leu Glu Ala
                165                 170                 175

Phe Gly Thr Ala Ile Leu Cys Leu Thr Val Leu Met Leu Ala Val Glu
            180                 185                 190

Lys His Arg Ala Thr Trp Phe Ala Pro Phe Val Ile Gly Ile Ala Leu
        195                 200                 205

Leu Ile Ala His Leu Ile Cys Ile Tyr Tyr Thr Gly Ala Gly Leu Asn
    210                 215                 220

Pro Ala Arg Ser Phe Gly Pro Ala Val Ala Ala Arg Ser Phe Pro Asn
225                 230                 235                 240

Tyr His Trp Ile Tyr Trp Leu Gly Pro Ile Leu Gly Ala Phe Leu Ala
                245                 250                 255

Tyr Ser Ile Trp Gln Met Trp Lys Trp Leu Asn Tyr Gln Thr Thr Asn
                260                 265                 270

Pro Gly Gln Asp Ser Asp Ala
            275

<210> SEQ ID NO 8
<211> LENGTH: 281
```

```
<212> TYPE: PRT
<213> ORGANISM: Spinacia oleracea

<400> SEQUENCE: 8

Met Ser Lys Glu Val Ser Glu Ala Gln Ala His Gln His Gly Lys
1               5                   10                  15

Asp Tyr Val Asp Pro Pro Ala Pro Phe Phe Asp Leu Gly Glu Leu
            20                  25                  30

Lys Leu Trp Ser Phe Trp Arg Ala Ala Ile Ala Glu Phe Ile Ala Thr
        35                  40                  45

Leu Leu Phe Leu Tyr Ile Thr Val Ala Thr Val Ile Gly His Ser Lys
    50                  55                  60

Glu Thr Val Val Cys Gly Ser Val Gly Leu Leu Gly Ile Ala Trp Ala
65              70                  75                  80

Phe Gly Gly Met Ile Phe Val Leu Val Tyr Cys Thr Ala Gly Ile Ser
                85                  90                  95

Gly Gly His Ile Asn Pro Ala Val Thr Phe Gly Leu Phe Leu Ala Arg
            100                 105                 110

Lys Val Ser Leu Leu Arg Ala Leu Val Tyr Met Ile Ala Gln Cys Leu
        115                 120                 125

Gly Ala Ile Cys Gly Val Gly Leu Val Lys Ala Phe Met Lys Gly Pro
    130                 135                 140

Tyr Asn Gln Phe Gly Gly Ala Asn Ser Val Ala Leu Gly Tyr Asn
145                 150                 155                 160

Lys Gly Thr Ala Leu Gly Ala Glu Ile Ile Gly Thr Phe Val Leu Val
                165                 170                 175

Tyr Thr Val Phe Ser Ala Thr Asp Pro Lys Arg Ser Ala Arg Asp Ser
            180                 185                 190

His Val Pro Ile Leu Ala Pro Leu Pro Ile Gly Phe Ala Val Phe Met
        195                 200                 205

Val His Leu Ala Thr Ile Pro Ile Thr Gly Thr Gly Ile Asn Pro Ala
    210                 215                 220

Arg Ser Phe Gly Ala Ala Val Ile Phe Asn Ser Asn Lys Val Trp Asp
225                 230                 235                 240

Asp Gln Trp Ile Phe Trp Val Gly Pro Phe Ile Gly Ala Ala Val Ala
                245                 250                 255

Ala Ala Tyr His Gln Tyr Val Leu Arg Ala Ala Ile Lys Ala Leu
            260                 265                 270

Gly Ser Phe Arg Ser Asn Pro Thr Asn
        275                 280

<210> SEQ ID NO 9
<211> LENGTH: 269
<212> TYPE: PRT
<213> ORGANISM: Homo sapiens

<400> SEQUENCE: 9

Met Ala Ser Glu Phe Lys Lys Lys Leu Phe Trp Arg Ala Val Val Ala
1               5                   10                  15

Glu Phe Leu Ala Thr Thr Leu Phe Val Phe Ile Ser Ile Gly Ser Ala
            20                  25                  30

Leu Gly Phe Lys Tyr Pro Val Gly Asn Asn Gln Thr Ala Val Gln Asp
        35                  40                  45

Asn Val Lys Val Ser Leu Ala Phe Gly Leu Ser Ile Ala Thr Leu Ala
    50                  55                  60
```

Gln Ser Val Gly His Ile Ser Gly Ala His Leu Asn Pro Ala Val Thr
65                  70                  75                  80

Leu Gly Leu Leu Leu Ser Cys Gln Ile Ser Ile Phe Arg Ala Leu Met
            85                  90                  95

Tyr Ile Ile Ala Gln Cys Val Gly Ala Ile Val Ala Thr Ala Ile Leu
            100                 105                 110

Ser Gly Ile Thr Ser Ser Leu Thr Gly Asn Ser Leu Gly Arg Asn Asp
            115                 120                 125

Leu Ala Asp Gly Val Asn Ser Gly Gln Gly Leu Gly Ile Glu Ile Ile
        130                 135                 140

Gly Thr Leu Gln Leu Val Leu Cys Val Leu Ala Thr Thr Asp Arg Arg
145                 150                 155                 160

Arg Arg Asp Leu Gly Gly Ser Ala Pro Leu Ala Ile Gly Leu Ser Val
            165                 170                 175

Ala Leu Gly His Leu Leu Ala Ile Asp Tyr Thr Gly Cys Gly Ile Asn
            180                 185                 190

Pro Ala Arg Ser Phe Gly Ser Ala Val Ile Thr His Asn Phe Ser Asn
            195                 200                 205

His Trp Ile Phe Trp Val Gly Pro Phe Ile Gly Ala Leu Ala Val
        210                 215                 220

Leu Ile Tyr Asp Phe Ile Leu Ala Pro Arg Ser Ser Asp Leu Thr Asp
225                 230                 235                 240

Arg Val Lys Val Trp Thr Ser Gly Gln Val Glu Glu Tyr Asp Leu Asp
            245                 250                 255

Ala Asp Asp Ile Asn Ser Arg Val Glu Met Lys Pro Lys
            260                 265

<210> SEQ ID NO 10
<211> LENGTH: 323
<212> TYPE: PRT
<213> ORGANISM: Homo sapiens

<400> SEQUENCE: 10

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
            85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
            115                 120                 125

Gly Ala Gly Ile Leu Tyr Leu Val Thr Pro Pro Ser Val Val Gly Gly
        130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
            165                 170                 175

```
Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
        195                 200                 205

Gly Ala Ser Met Asn Pro Ala Arg Ser Phe Gly Pro Ala Val Ile Met
210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
                260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
290                 295                 300

Asp Arg Gly Glu Glu Lys Lys Gly Lys Asp Gln Ser Gly Glu Val Leu
305                 310                 315                 320

Ser Ser Val

<210> SEQ ID NO 11
<211> LENGTH: 295
<212> TYPE: PRT
<213> ORGANISM: Homo sapiens

<400> SEQUENCE: 11

Met Gln Pro Glu Gly Ala Glu Lys Gly Lys Ser Phe Lys Gln Arg Leu
1               5                   10                  15

Val Leu Lys Ser Ser Leu Ala Lys Glu Thr Leu Ser Glu Phe Leu Gly
                20                  25                  30

Thr Phe Ile Leu Ile Val Leu Gly Cys Gly Cys Val Ala Gln Ala Ile
            35                  40                  45

Leu Ser Arg Gly Arg Phe Gly Gly Val Ile Thr Ile Asn Val Gly Phe
50                  55                  60

Ser Met Ala Val Ala Met Ala Ile Tyr Val Ala Gly Gly Val Ser Gly
65                  70                  75                  80

Gly His Ile Asn Pro Ala Val Ser Leu Ala Met Cys Leu Phe Gly Arg
                85                  90                  95

Met Lys Trp Phe Lys Leu Pro Phe Tyr Val Gly Ala Gln Phe Leu Gly
            100                 105                 110

Ala Phe Val Gly Ala Ala Thr Val Phe Gly Ile Tyr Tyr Asp Gly Leu
        115                 120                 125

Met Ser Phe Ala Gly Gly Lys Leu Leu Ile Val Gly Glu Asn Ala Thr
130                 135                 140

Ala His Ile Phe Ala Thr Tyr Pro Ala Pro Tyr Leu Ser Leu Ala Asn
145                 150                 155                 160

Ala Phe Ala Asp Gln Val Val Ala Thr Met Ile Leu Leu Ile Ile Val
                165                 170                 175

Phe Ala Ile Phe Asp Ser Arg Asn Leu Gly Ala Pro Arg Gly Leu Glu
            180                 185                 190

Pro Ile Ala Ile Gly Leu Leu Ile Ile Val Ile Ala Ser Ser Leu Gly
        195                 200                 205

Leu Asn Ser Gly Cys Ala Met Asn Pro Ala Arg Asp Leu Ser Pro Arg
210                 215                 220
```

Leu Phe Thr Ala Leu Ala Gly Trp Gly Phe Glu Val Phe Arg Ala Gly
225                 230                 235                 240

Asn Asn Phe Trp Trp Ile Pro Val Val Gly Pro Leu Val Gly Ala Val
            245                 250                 255

Ile Gly Gly Leu Ile Tyr Val Leu Val Ile Glu Ile His His Pro Glu
        260                 265                 270

Pro Asp Ser Val Phe Lys Thr Glu Gln Ser Glu Asp Lys Pro Glu Lys
    275                 280                 285

Tyr Glu Leu Ser Val Ile Met
    290                 295

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (octyl)Gly
<220> FEATURE:
<221> NAME/KEY: MOD_RES
<222> LOCATION: (7)..(7)
<223> OTHER INFORMATION: (octyl)Gly
<220> FEATURE:
<221> NAME/KEY: MOD_RES
<222> LOCATION: (9)..(9)
<223> OTHER INFORMATION: (propargyl)Gly

<400> SEQUENCE: 12

Xaa Ser Leu Ser Leu Asp Xaa Asp Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: azidohomoalanine
<220> FEATURE:
<221> NAME/KEY: MOD_RES
<222> LOCATION: (2)..(2)
<223> OTHER INFORMATION: (octyl)Gly
<220> FEATURE:
<221> NAME/KEY: MOD_RES
<222> LOCATION: (8)..(8)
<223> OTHER INFORMATION: (octyl)Gly

<400> SEQUENCE: 13

Xaa Xaa Ser Leu Ser Leu Asp Xaa Asp
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (propargyl)Gly
<220> FEATURE:
<221> NAME/KEY: MOD_RES

```
<222> LOCATION: (2)..(2)
<223> OTHER INFORMATION: (octyl)Gly
<220> FEATURE:
<221> NAME/KEY: MOD_RES
<222> LOCATION: (8)..(8)
<223> OTHER INFORMATION: (octyl)Gly

<400> SEQUENCE: 14

Xaa Xaa Ser Leu Ser Leu Asp Xaa Asp
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (octyl)Gly
<220> FEATURE:
<221> NAME/KEY: MOD_RES
<222> LOCATION: (5)..(5)
<223> OTHER INFORMATION: amino hexenoic acid
<220> FEATURE:
<221> NAME/KEY: MOD_RES
<222> LOCATION: (8)..(8)
<223> OTHER INFORMATION: (octyl)Gly

<400> SEQUENCE: 15

Xaa Ser Leu Ser Xaa Leu Asp Xaa Asp Gly Leu
1               5                   10

<210> SEQ ID NO 16
<211> LENGTH: 6003
<212> TYPE: DNA
<213> ORGANISM: Artificial Sequence
<220> FEATURE:
<223> OTHER INFORMATION: Plasmid used for expression of AqpZ in
      Eschericia coli.

<400> SEQUENCE: 16
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttta     180
atcacgcttt tccagcaggg tccggtaaat cagaccaccg ataatgccgc cgacaattgg     240
caccacccag aagaaccaca gttgttctaa tgcccagccg ccctggaaga tagcaaccgc     300
ggtgctgcgc gccgggttaa cagaagtgtt agtcaccgga atactaatta agtgaatcag     360
ggttaaggcc agaccaatag cgatcggcgc aaaacctgcc ggcgcgaatt tgtcggttgc     420
gccgtggatc accaacagga aacctgcact caataccagt tcaactacca gcgcggaaag     480
catggaataa ccgcctggtg aatgctcgcc ataaccgtta gaagcaaaac cgctggctgc     540
cgcgtcaaaa cccgttttac cactggcaat taaatacagc agcgccgctg caacaatacc     600
gccgacaacc tgggcaatta cgtagccaac gacttctttt gccggaaaac gtccgccagc     660 ccataaaacca atagtgaccg ccgggttaaa atgaccacca gaaatatgac caacagcaaa     720
ggccatcgtc agaacggtca gaccgaacgc caacgccacg ccggcaaaac caatgcctaa     780
ttccgggaag cctgcggcca gtacagcact accacagcca ccaaaaacaa gccagaaagt     840
accaaaacat tcagctgcta atttctgaa  catatggctg ccgcgcggca ccaggccgct     900
gctgtgatga tgatgatgat ggctgctgcc catggtatat ctccttctta aagttaaaca     960
```

```
aaattatttc tagaggggaa ttgttatccg ctcacaattc ccctatagtg agtcgtatta   1020
atttcgcggg atcgagatct cgatcctcta cgccggacgc atcgtggccg gcatcaccgg   1080
cgccacaggt gcggttgctg gcgcctatat cgccgacatc accgatgggg aagatcgggc   1140
tcgccacttc gggctcatga gcgcttgttt cggcgtgggt atggtggcag gccccgtggc   1200
cgggggactg ttgggcgcca tctccttgca tgcaccattc cttgcggcgg cggtgctcaa   1260
cggcctcaac ctactactgg gctgcttcct aatgcaggag tcgcataagg gagagcgtcg   1320
agatcccgga caccatcgaa tggcgcaaaa cctttcgcgg tatggcatga tagcgcccgg   1380
aagagagtca attcagggtg gtgaatgtga aaccagtaac gttatacgat gtcgcagagt   1440
atgccggtgt ctcttatcag accgtttccc gcgtggtgaa ccaggccagc cacgtttctg   1500
cgaaaacgcg ggaaaaagtg gaagcggcga tggcggagct gaattacatt cccaaccgcg   1560
tggcacaaca actggcgggc aaacagtcgt tgctgattgg cgttgccacc tccagtctgg   1620
ccctgcacgc gccgtcgcaa attgtcgcgg cgattaaatc tcgcgccgat caactgggtg   1680
ccagcgtggt ggtgtcgatg gtagaacgaa gcggcgtcga agcctgtaaa gcggcggtgc   1740
acaatcttct cgcgcaacgc gtcagtgggc tgatcattaa ctatccgctg gatgaccagg   1800
atgccattgc tgtggaagct gcctgcacta atgttccggc gttatttctt gatgtctctg   1860
accagacacc catcaacagt attattttct cccatgaaga cggtacgcga ctgggcgtgg   1920
agcatctggt cgcattgggt caccagcaaa tcgcgctgtt agcgggccca ttaagttctg   1980
tctcggcgcg tctgcgtctg gctggctggc ataaatatct cactcgcaat caaattcagc   2040
cgatagcgga acgggaaggc gactggagtg ccatgtccgg ttttcaacaa accatgcaaa   2100
tgctgaatga gggcatcgtt cccactgcga tgctggttgc caacgatcag atggcgctgg   2160
gcgcaatgcg cgccattacc gagtccgggc tgcgcgttgg tgcggatatc tcggtagtgg   2220
gatacgacga taccgaagac agctcatgtt atatcccgcc gttaaccacc atcaaacagg   2280
attttcgcct gctggggcaa accagcgtgg accgcttgct gcaactctct cagggccagg   2340
cggtgaaggg caatcagctg ttgcccgtct cactggtgaa aagaaaaacc accctggcgc   2400
ccaatacgca aaccgcctct ccccgcgcgt tggccgattc attaatgcag ctggcacgac   2460
aggtttcccg actggaaagc gggcagtgag cgcaacgcaa ttaatgtaag ttagctcact   2520
cattaggcac cgggatctcg accgatgccc ttgagagcct tcaacccagt cagctccttc   2580
cggtgggcgc ggggcatgac tatcgtcgcc gcacttatga ctgtcttctt tatcatgcaa   2640
ctcgtaggac aggtgccggc agcgctctgg gtcattttcg gcgaggaccg ctttcgctgg   2700
agcgcgacga tgatcggcct gtcgcttgcg gtattcggaa tcttgcacgc cctcgctcaa   2760
gccttcgtca ctggtcccgc caccaaacgt ttcggcgaga agcaggccat tatcgccggc   2820
atggcggccc cacgggtgcg catgatcgtg ctcctgtcgt tgaggacccg gctaggctgg   2880
cggggttgcc ttactggtta gcagaatgaa tcaccgatac gcgagcgaac gtgaagcgac   2940
tgctgctgca aaacgtctgc gacctgagca acaacatgaa tggtcttcgg tttccgtgtt   3000
tcgtaaagtc tggaaacgcg gaagtcagcg ccctgcacca ttatgttccg gatctgcatc   3060
gcaggatgct gctggctacc ctgtggaaca cctacatctg tattaacgaa gcgctggcat   3120
tgaccctgag tgattttttct ctggtcccgc cgcatccata ccgccagttg tttaccctca   3180
caacgttcca gtaaccgggc atgttcatca tcagtaaccc gtatcgtgag catcctctct   3240
cgtttcatcg gtatcattac ccccatgaac agaaatcccc cttacacgga ggcatcagtg   3300
```

```
accaaacagg aaaaaaccgc ccttaacatg gcccgcttta tcagaagcca gacattaacg    3360
cttctggaga aactcaacga gctggacgcg gatgaacagg cagacatctg tgaatcgctt    3420
cacgaccacg ctgatgagct ttaccgcagc tgcctcgcgc gtttcggtga tgacggtgaa    3480
aacctctgac acatgcagct cccggagacg gtcacagctt gtctgtaagc ggatgccggg    3540
agcagacaag cccgtcaggg cgcgtcagcg ggtgttggcg ggtgtcgggg cgcagccatg    3600
acccagtcac gtagcgatag cggagtgtat actggcttaa ctatgcggca tcagagcaga    3660
ttgtactgag agtgcaccat atatgcggtg tgaaataccg cacagatgcg taaggagaaa    3720
ataccgcatc aggcgctctt ccgcttcctc gctcactgac tcgctgcgct cggtcgttcg    3780
gctgcggcga gcggtatcag ctcactcaaa ggcggtaata cggttatcca cagaatcagg    3840
ggataacgca ggaaagaaca tgtgagcaaa aggccagcaa aaggccagga accgtaaaaa    3900
ggccgcgttg ctggcgtttt tccataggct ccgcccccct gacgagcatc acaaaaatcg    3960
acgctcaagt cagaggtggc gaaacccgac aggactataa agataccagg cgtttccccc    4020
tggaagctcc ctcgtgcgct ctcctgttcc gaccctgccg cttaccggat acctgtccgc    4080
ctttctccct tcgggaagcg tggcgctttc tcatagctca cgctgtaggt atctcagttc    4140
ggtgtaggtc gttcgctcca agctgggctg tgtgcacgaa ccccccgttc agcccgaccg    4200
ctgcgcctta tccggtaact atcgtcttga gtccaacccg gtaagacacg acttatcgcc    4260
actggcagca gccactggta acaggattag cagagcgagg tatgtaggcg gtgctacaga    4320
gttcttgaag tggtggccta actacggcta cactagaagg acagtatttg gtatctgcgc    4380
tctgctgaag ccagttacct tcggaaaaag agttggtagc tcttgatccg gcaaacaaac    4440
caccgctggt agcggtggtt tttttgtttg caagcagcag attacgcgca gaaaaaaagg    4500
atctcaagaa gatcctttga tcttttctac ggggtctgac gctcagtgga acgaaaactc    4560
acgttaaggg attttggtca tgaacaataa aactgtctgc ttacataaac agtaatacaa    4620
ggggtgttat gagccatatt caacgggaaa cgtcttgctc taggccgcga ttaaattcca    4680
acatggatgc tgatttatat gggtataaat gggctcgcga taatgtcggg caatcaggtg    4740
cgacaatcta tcgattgtat gggaagcccg atgcgccaga gttgtttctg aaacatggca    4800
aaggtagcgt tgccaatgat gttacagatg agatggtcag actaaactgg ctgacggaat    4860
ttatgcctct tccgaccatc aagcatttta tccgtactcc tgatgatgca tggttactca    4920
ccactgcgat ccccgggaaa acagcattcc aggtattaga agaatatcct gattcaggtg    4980
aaaatattgt tgatgcgctg gcagtgttcc tgcgccggtt gcattcgatt cctgtttgta    5040
attgtccttt taacagcgat cgcgtatttc gtctcgctca ggcgcaatca cgaatgaata    5100
acggtttggt tgatgcgagt gattttgatg acgagcgtaa tggctggcct gttgaacaag    5160
tctggaaaga aatgcataaa cttttgccat tctcaccgga ttcagtcgtc actcatggtg    5220
atttctcact tgataacctt attttgacg aggggaaatt aataggttgt attgatgttg    5280
gacgagtcgg aatcgcagac cgataccagg atcttgccat cctatggaac tgcctcggtg    5340
agttttctcc ttcattacag aaacggcttt ttcaaaaata tggtattgat aatcctgata    5400
tgaataaatt gcagtttcat ttgatgctcg atgagttttt ctaagaatta attcatgagc    5460
ggatacatat ttgaatgtat ttagaaaaat aaacaaatag gggttccgcg cacatttccc    5520
cgaaaagtgc cacctgaaat tgtaaacgtt aatattttgt taaaattcgc gttaaatttt    5580
tgttaaatca gctcatttt taaccaatag gccgaaatcg gcaaaatccc ttataaatca    5640
aaagaataga ccgagatagg gttgagtgtt gttccagttt ggaacaagag tccactatta    5700
```

```
aagaacgtgg actccaacgt caaagggcga aaaaccgtct atcagggcga tggcccacta    5760
cgtgaaccat caccctaatc aagtttttg gggtcgaggt gccgtaaagc actaaatcgg    5820
aaccctaaag ggagccccg atttagagct tgacggggaa agccggcgaa cgtggcgaga    5880
aaggaaggga agaaagcgaa aggagcgggc gctagggcgc tggcaagtgt agcggtcacg    5940
ctgcgcgtaa ccaccacacc cgccgcgctt aatgcgccgc tacagggcgc gtcccattcg    6000
cca                                                                  6003
```